United States Patent
Cruz-Acuna et al.

(10) Patent No.: US 11,478,571 B2
(45) Date of Patent: Oct. 25, 2022

(54) SYNTHETIC HYDROGEL CARRIERS FOR CELLULAR STRUCTURES, GENERATION OF ORGANOIDS, AND TREATMENT OF TISSUE INJURY

(71) Applicants: GEORGIA TECH RESEARCH CORPORATION, Atlanta, GA (US); THE REGENTS OF THE UNIVERSITY OF MICHIGAN, Ann Arbor, MI (US)

(72) Inventors: Ricardo Cruz-Acuna, Atlanta, GA (US); Andres J. Garcia, Atlanta, GA (US); Asma Nusrat, Ann Arbor, MI (US); Jason R. Spence, Ann Arbor, MI (US); Miguel Quiros, Ann Arbor, MI (US)

(73) Assignees: Georgia Tech Research Corporation, Atlanta, GA (US); The Regents of the University of Michigan, Ann Arbor, MI (US)

( * ) Notice: Subject to any disclaimer, the term of this patent is extended or adjusted under 35 U.S.C. 154(b) by 256 days.

(21) Appl. No.: 16/492,263

(22) PCT Filed: Mar. 9, 2018

(86) PCT No.: PCT/US2018/021771
§ 371 (c)(1),
(2) Date: Sep. 9, 2019

(87) PCT Pub. No.: WO2018/165565
PCT Pub. Date: Sep. 13, 2018

(65) Prior Publication Data
US 2020/0078493 A1    Mar. 12, 2020

Related U.S. Application Data

(60) Provisional application No. 62/469,299, filed on Mar. 9, 2017.

(51) Int. Cl.
| | |
|---|---|
| *A61L 27/52* | (2006.01) |
| *A61K 35/28* | (2015.01) |
| *A61K 35/38* | (2015.01) |
| *A61K 35/50* | (2015.01) |
| *A61K 35/545* | (2015.01) |
| *A61L 27/38* | (2006.01) |

(52) U.S. Cl.
CPC .............. *A61L 27/52* (2013.01); *A61K 35/28* (2013.01); *A61K 35/38* (2013.01); *A61K 35/50* (2013.01); *A61K 35/545* (2013.01); *A61L 27/3834* (2013.01); *A61L 27/3886* (2013.01); *A61L 2300/252* (2013.01)

(58) Field of Classification Search
CPC ................................ A61L 35/28; A61K 35/28
See application file for complete search history.

(56) References Cited

U.S. PATENT DOCUMENTS

| | | | |
|---|---|---|---|
| 2013/0052712 A1* | 2/2013 | Cha | ...................... C12N 5/0654 435/177 |
| 2015/0071997 A1 | 3/2015 | Garcia et al. | |

FOREIGN PATENT DOCUMENTS

| | | |
|---|---|---|
| WO | 01/24842 | 4/2001 |
| WO | 2017/037295 | 3/2017 |

OTHER PUBLICATIONS

Shekaran et al. Biomaterials (2014), 35(21); 5453-5461.*
International Search Report and Written Opinion dated Jun. 15, 2018, from International Application No. PCT/US2018/021771, 20 pages.
Gjorevski, N. et al. "Designer matrices for intestinal stem cell and organoid culture", Nature, vol. 539, Nov. 2016, 17 pages.
Enemchukwu, N. et al. "Synthetic matrices reveal contributions of ECM biophysical and biochemical properties to epithelial morphogenesis", JCB: Tools, Dec. 2015, 12 pages.
Cruz-Acuna, R. et al. "Synthetic Hydrogels for Human Intestinal Organoid Generation and Colonic Wound Repair", Nat Cell Biol. Nov. 2017; 19(11): 1326-1335.

* cited by examiner

*Primary Examiner* — Jeanette M Lieb
(74) *Attorney, Agent, or Firm* — Meunier Carlin & Curfman LLC

(57) ABSTRACT

Disclosed herein are synthetic hydrogel useful for the generation, storage and administration of cellular structures such as spheroids and organoids.

19 Claims, 30 Drawing Sheets
Specification includes a Sequence Listing.

SEQUENCE LISTING

```
<160> NUMBER OF SEQ ID NOS: 57

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1

Gly Arg Gly Asp Ser Pro Cys
1               5

<210> SEQ ID NO 2
```

```
<211> LENGTH: 5
<212> TYPE: PRT
<213> ORGANISM: Artificial Sequence
<220> FEATURE:
<223> OTHER INFORMATION: Synthetic construct

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Cys Arg Gly Asp Ser Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct

<400> SEQUENCE: 4

Cys Pro His Ser Arg Asn
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Cys Gly Trp Gly Gly Arg Gly Asp Ser Pro
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

Cys Gly Gly Ser Ile Asp Gln Val Glu Pro Tyr Ser Ser Thr Ala Gln
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic construct

<400> SEQUENCE: 7

Cys Gly Gly Arg Asn Ile Ala Glu Ile Ile Lys Asp Ile
1               5                   10

<210> SEQ ID NO 8
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 8

Cys Gly Gly Asp Ile Thr Tyr Val Arg Leu Lys Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Cys Gly Gly Asp Ile Thr Val Thr Leu Asn Arg Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

Cys Gly Gly Arg Tyr Val Val Leu Pro Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Cys Gly Gly Lys Ala Phe Asp Ile Thr Tyr Val Arg Leu Lys Phe
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Cys Gly Gly Glu Gly Tyr Gly Glu Gly Tyr Ile Gly Ser Arg
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (16)..(16)
<223> OTHER INFORMATION: Xaa can be any naturally occurring amino acid

<400> SEQUENCE: 13

Cys Gly Gly Ala Thr Leu Gln Leu Gln Glu Gly Arg Leu His Phe Xaa
1               5                   10                  15
```

Phe Asp Leu Gly Lys Gly Arg
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic construct

<400> SEQUENCE: 14

Cys Gly Gly Ser Tyr Trp Tyr Arg Ile Glu Ala Ser Arg Thr Gly
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Cys Gly Gly Gly Glu Phe Tyr Phe Asp Leu Arg Leu Lys Gly Asp Lys
1               5                   10                  15

Tyr

<210> SEQ ID NO 16
<211> LENGTH: 16
<212> TYPE: PRT
<213> ORGANISM: Artificial Sequence
<220> FEATURE:
<223> OTHER INFORMATION: Synthetic construct

<400> SEQUENCE: 16

Cys Lys Gly Gly Asn Gly Glu Pro Arg Gly Asp Thr Tyr Arg Ala Tyr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Cys Lys Gly Gly Pro Gln Val Thr Arg Gly Asp Val Phe Thr Met Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Cys Gly Gly Asn Arg Trp His Ser Ile Tyr Ile Thr Arg Phe Gly
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic construct

<400> SEQUENCE: 19

Cys Gly Gly Ala Ser Ile Lys Val Ala Val Ser Ala Asp Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct

<400> SEQUENCE: 20

Cys Gly Gly Thr Thr Val Lys Tyr Ile Phe Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic construct

<400> SEQUENCE: 21

Cys Gly Gly Ser Ile Lys Ile Arg Gly Thr Tyr Ser
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Cys Gly Gly Ser Ile Asn Asn Asn Arg
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic construct

<400> SEQUENCE: 23

Cys Gly Gly Ser Asp Pro Gly Tyr Ile Gly Ser Arg
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic construct

<400> SEQUENCE: 24

Cys Tyr Ile Gly Ser Arg
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic construct

```
<400> SEQUENCE: 25

Cys Gly Gly Thr Pro Gly Pro Gln Gly Ile Ala Gly Gln Gly Val Val
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Cys Gly Gly Thr Pro Gly Pro Gln Gly Ile Ala Gly Gln Arg Val Val
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Cys Gly Gly Met Asn Tyr Tyr Ser Asn Ser
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic construct

<400> SEQUENCE: 28

Cys Gly Gly Lys Lys Gln Arg Phe Arg His Arg Asn Arg Lys Gly
1               5                   10                  15

<210> SEQ ID NO 29
<211> LENGTH: 22
<212> TYPE: PRT
<213> ORGANISM: Artificial Sequence
<220> FEATURE:
<223> OTHER INFORMATION: Synthetic construct

<400> SEQUENCE: 29

Cys Arg Gly Asp Gly Gly Gly Gly Gly Gly Gly Gly Gly Gly Gly Gly
1               5                   10                  15

Gly Pro His Ser Arg Asn
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic construct

<400> SEQUENCE: 30

Cys Pro His Ser Arg Asn Ser Gly Ser Gly Ser Gly Ser Gly Ser Gly
1               5                   10                  15

Arg Gly Asp

<210> SEQ ID NO 31
<211> LENGTH: 20
<212> TYPE: PRT
```

```
<213> ORGANISM: Artificial Sequence
<220> FEATURE:
<223> OTHER INFORMATION: Synthetic construct

<400> SEQUENCE: 31

Ala Cys Glu Thr Tyr Leu Ala Thr Glu Asp Gly Cys Tyr Gly Arg Gly
1               5                   10                  15

Asp Ser Pro Gly
            20

<210> SEQ ID NO 32
<211> LENGTH: 6
<212> TYPE: PRT
<213> ORGANISM: Artificial Sequence
<220> FEATURE:
<223> OTHER INFORMATION: Synthetic construct

<400> SEQUENCE: 32

Gly Pro Pro Gly Pro Cys
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Cys Arg Asp Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic construct

<400> SEQUENCE: 34

Cys Tyr Cys Leu Ile Cys Arg Gly Asp Phe Asp Cys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic construct

<400> SEQUENCE: 35

Cys Gly Gly Arg Lys Arg Leu Gln Val Gln Leu Ser Ile Arg Thr
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: Synthetic construct

<400> SEQUENCE: 36

Cys Ile Lys Val Ala Val
1               5

<210> SEQ ID NO 37
```

```
<211> LENGTH: 15
<212> TYPE: PRT
<213> ORGANISM: Artificial Sequence
<220> FEATURE:
<223> OTHER INFORMATION: Synthetic construct

<400> SEQUENCE: 37

Cys Gly Gly Ala Ala Ser Ile Lys Val Ala Val Ser Ala Asp Arg
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Cys Gly Gly Lys Arg Thr Gly Gln Tyr Lys Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct

<400> SEQUENCE: 39

Cys Gly Gly Thr Tyr Arg Ser Arg Lys Tyr
1               5                   10

<210> SEQ ID NO 40
<211> LENGTH: 25
<212> TYPE: PRT
<213> ORGANISM: Artificial Sequence
<220> FEATURE:
<223> OTHER INFORMATION: Synthetic construct; X at position 14 is
      hydroxyproline
<220> FEATURE:
<221> NAME/KEY: misc_feature
<222> LOCATION: (14)..(14)
<223> OTHER INFORMATION: Xaa can be any naturally occurring amino acid

<400> SEQUENCE: 40

Cys Gly Gly Tyr Gly Gly Pro Gly Pro Pro Gly Phe Xaa Gly Glu
1               5                   10                  15

Arg Pro Pro Gly Pro Pro Gly Pro Cys
            20                  25

<210> SEQ ID NO 41
<211> LENGTH: 20
<212> TYPE: PRT
<213> ORGANISM: Artificial Sequence
<220> FEATURE:
<223> OTHER INFORMATION: Synthetic construct

<400> SEQUENCE: 41

Cys Gly Gly Lys Arg Thr Gly Gln Tyr Lys Leu Gly Ser Lys Thr Gly
1               5                   10                  15

Pro Gly Gln Lys
            20

<210> SEQ ID NO 42
<211> LENGTH: 14
<212> TYPE: PRT
<213> ORGANISM: Artificial Sequence
```

```
<220> FEATURE:
<223> OTHER INFORMATION: Synthetic construct

<400> SEQUENCE: 42

Gln Ala Lys His Lys Gln Arg Lys Arg Leu Lys Ser Ser Cys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic construct

<400> SEQUENCE: 43

Ser Pro Lys His His Ser Gln Arg Ala Arg Lys Lys Lys Asn Lys Asn
1               5                   10                  15

Cys

<210> SEQ ID NO 44
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 44

Cys Gly Gly Xaa Asx Asx Xaa Asx Xaa
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 45

Cys Gly Gly Xaa Asx Asx Asx Xaa Xaa Asx Xaa
1               5                   10

<210> SEQ ID NO 46
<211> LENGTH: 16
<212> TYPE: PRT
<213> ORGANISM: Artificial Sequence
<220> FEATURE:
```

<223> OTHER INFORMATION: Synthetic construct

<400> SEQUENCE: 46

Gly Cys Arg Asp Gly Pro Gln Gly Ile Trp Gly Gln Asp Arg Cys Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic construct

<400> SEQUENCE: 47

Gly Cys Arg Asp Gly Pro Gln Gly Ile Ala Gly Gln Asp Arg Cys Gly
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic construct

<400> SEQUENCE: 48

Gly Cys Arg Asp Val Pro Met Ser Met Arg Gly Gly Asp Arg Cys Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

Gly Cys Arg Asp Ile Pro Val Ser Leu Arg Ser Gly Asp Arg Cys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic construct

<400> SEQUENCE: 50

Gly Cys Arg Asp Arg Pro Phe Ser Met Ile Met Gly Asp Arg Cys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic construct

<400> SEQUENCE: 51

Gly Cys Arg Asp Val Pro Leu Ser Leu Thr Met Gly Asp Arg Cys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic construct

```
<400> SEQUENCE: 52

Gly Cys Arg Asp Val Pro Leu Ser Leu Tyr Ser Gly Asp Arg Cys Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic construct

<400> SEQUENCE: 53

Gly Cys Arg Asp Ile Pro Glu Ser Leu Arg Ala Gly Asp Arg Cys Gly
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Synthetic construct

<400> SEQUENCE: 54

Gly Cys Arg Asp Ser Gly Glu Ser Pro Ala Tyr Tyr Thr Ala Asp Arg
1               5                   10                  15

Cys Gly

<210> SEQ ID NO 55
<211> LENGTH: 18
<212> TYPE: PRT
<213> ORGANISM: Artificial Sequence
<220> FEATURE:
<223> OTHER INFORMATION: Synthetic construct

<400> SEQUENCE: 55

Gly Cys Arg Asp Gly Gly Tyr Ala Glu Leu Arg Met Gly Gly Asp Arg
1               5                   10                  15

Cys Gly

<210> SEQ ID NO 56
<211> LENGTH: 18
<212> TYPE: PRT
<213> ORGANISM: Artificial Sequence
<220> FEATURE:
<223> OTHER INFORMATION: Synthetic construct

<400> SEQUENCE: 56

Gly Cys Arg Asp Gly Gly Pro Leu Gly Leu Tyr Ala Gly Gly Asp Arg
1               5                   10                  15

Cys Gly

<210> SEQ ID NO 57
<211> LENGTH: 16
<212> TYPE: PRT
<213> ORGANISM: Artificial Sequence
<220> FEATURE:
<223> OTHER INFORMATION: Synthetic construct

<400> SEQUENCE: 57

Gly Cys Arg Asp Gly Pro Leu Gly Leu Trp Ala Arg Asp Arg Cys Gly
1               5                   10                  15
```

SYNTHETIC HYDROGEL CARRIERS FOR CELLULAR STRUCTURES, GENERATION OF ORGANOIDS, AND TREATMENT OF TISSUE INJURY

CROSS REFERENCE TO RELATED APPLICATION

This application claims the benefit of U.S. Provisional Application 62/469,299, filed on Mar. 9, 2017, the contents of which are hereby incorporated in its entirety.

STATEMENT OF GOVERNMENT SUPPORT

This invention was made with government support under R01 AR062368, R01 AR062920, R01 DK055679, R01 DK059888, DK055679, DK059888, and DK089763, awarded by the National Institutes of Health. The government has certain rights in the invention.

FIELD OF THE INVENTION

The invention is directed to synthetic hydrogels useful as storage and growth matrices for cellular structures, and as delivery vehicles in compositions useful for tissue and wound repair.

BACKGROUND

Human pluripotent stem cells (hPSCs), such as embryonic stem cells (ESCs) and induced pluripotent stem cells (iPSCs), are important cell sources for regenerative therapies and modeling of human diseases. In vitro generation of human organoids from hPSCs offers unparalleled strategies for generating multi-cellular 3D structures recapitulating important features of epithelial and mesenchymal tissues. For example, human intestinal organoid (HIO) technology provides a powerful platform for functional modeling and repair of genetic defects in human intestinal development and the establishment of chronic disease models, such as inflammatory bowel disease.

In order to generate HIOs, hPSCs have cultured and differentiated using growth factors in a Matrigel™-coated substrate, giving rise to 3D intestinal spheroids which are collected and encapsulated within Matrigel™ for expansion into HIOs. Matrigel™ is a heterogeneous, complex mixture of ECM proteins, proteoglycans, and growth factors secreted by Engelbreth-Holm-Swarm mouse sarcoma cells, which is required for 3D growth and expansion of HIOs. There are substantial limitations associated with Matrigel™, as it suffers from lot-to-lot compositional and structural variability. Importantly, this tumor-derived matrix has limited potential for use in a clinical context.

There remains a need for improved carriers for organoids and other cellular structures. There remains a need for improved methods to generate human organoids, including intestinal organoids. The remains a need for methods to generate intestinal organoids spheroids that do not require the use of Matrigel™. There also remains a need for improved methods of treating injuries, including mucosal wounds.

SUMMARY

Disclosed herein is a completely synthetic hydrogel that supports in vitro generation of organoids from spheroids without Matrigel™ encapsulation. The synthetic hydrogels are also useful as a storage matrix for spheroids and organoids, and as vehicles for the administration of such organoids and spheroids to a subject. The synthetic hydrogel promotes organoid engraftment and healing of injuries, including mucosal wounds. The synthetic hydrogel can also be used as an injectable vehicle to deliver organoids and other therapeutics to injuries.

The details of one or more embodiments are set forth in the descriptions below. Other features, objects, and advantages will be apparent from the description and from the claims.

DETAILED DESCRIPTION

Figure 1A:
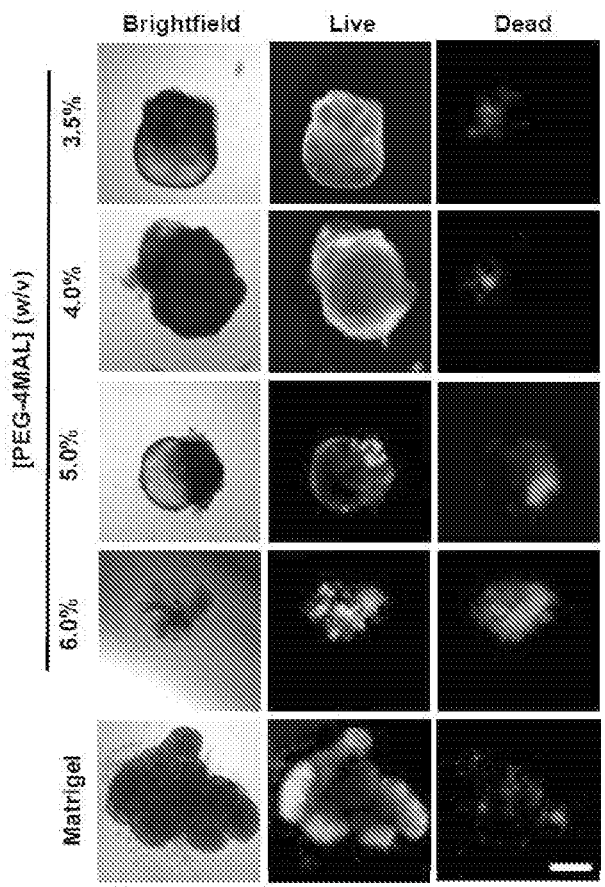
FIG. 1A depicts transmitted light and fluorescence microscopy images of HIOs cultured in PEG-4MAL hydrogels of different polymer density or Matrigel™. HIO viability was assessed by Calcein-AM (live)/TOTO-3 iodide (dead) labeling at 7 d after encapsulation. Bar, 500 µm.
Figure 1B:
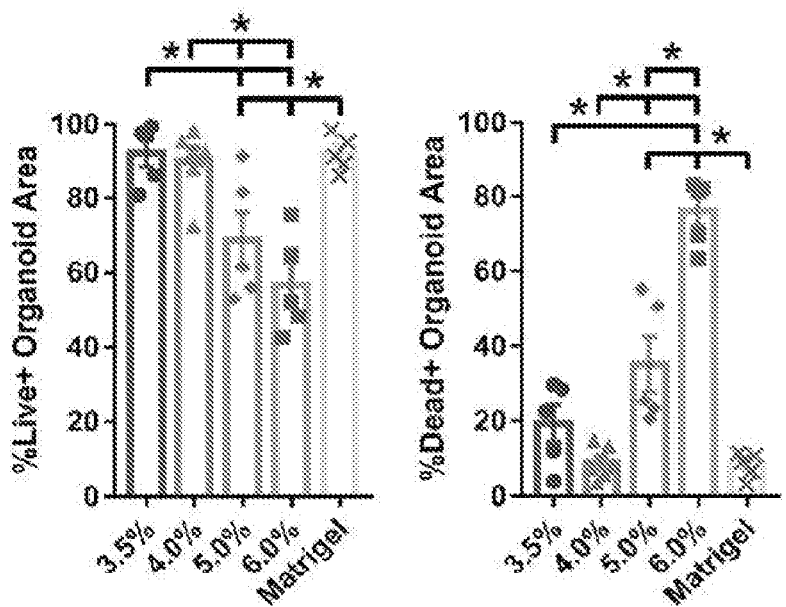
FIG. 1B depicts percentage of total organoid area stained for live or dead (mean±SEM) after 7 d of encapsulation (n=5 or 6 organoids analyzed per condition). One-way ANOVA with Tukey's multiple comparisons test showed significant differences between 4.0% PEG-4MAL or Matrigel™ and 5.0 or 6.0% PEG-4MAL ($*P<0.05$, $P<0.01$, $*P<0.001$, $****P<0.0001$). Graphs and images are representative of one and three independent experiments, respectively, performed with 6 PEG-4MAL/Matrigel™ per condition.
Figure 2A:
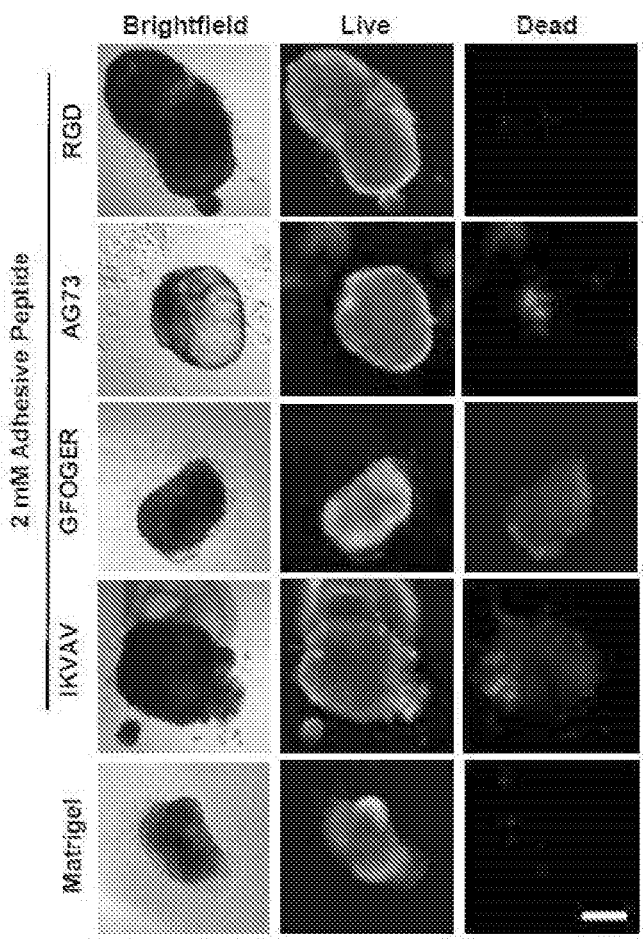
FIG. 2A depicts transmitted light and fluorescence microscopy images of HIOs cultured in 4.0% PEG-4MAL hydrogels functionalized with different adhesive peptides or Matrigel™. HIO viability was assessed at 7 d after encapsulation. Bar, 500 µm.
Figure 2B:
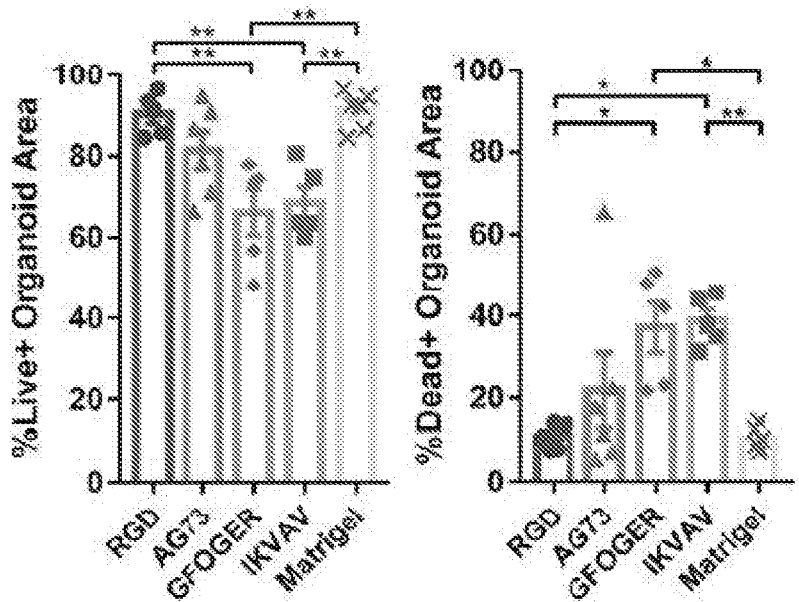
FIG. 2B depicts percentage of total organoid area stained for live or dead (mean±SEM) after 7 d of encapsulation (n=5 or 6 organoids analyzed per condition). One-way ANOVA with Tukey's multiple comparisons test showed significant differences between PEG-4MAL-RGD or Matrigel™ and PEG-4MAL-GFOGER or -IKVAV ($*P<0.05$, $**P<0.01$). Graphs and images are representative of one and three independent experiments, respectively, performed with 6 PEG-4MAL/Matrigel™ per condition.
Figure 3A:
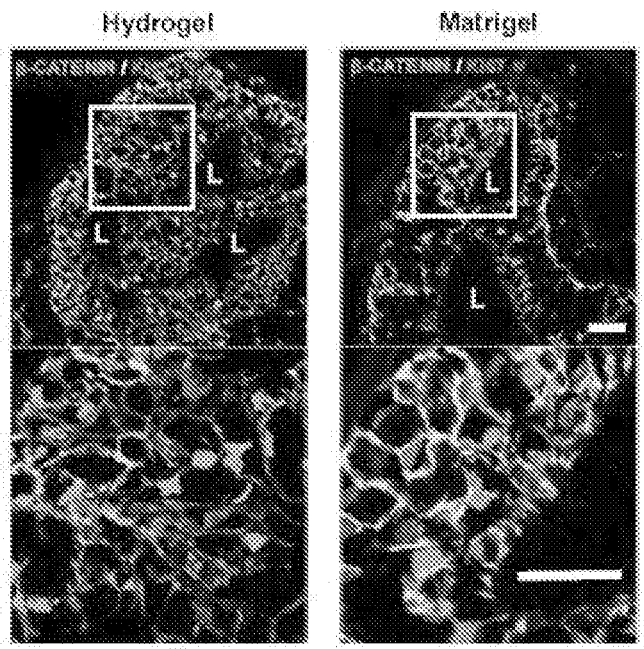
FIG. 3A and FIG. 3B depict fluorescence microscopy images of a HIO at 7 d after encapsulation in 4.0% PEG-4MAL-RGD hydrogel or Matrigel™, and labeled for FIG. 3A, β-CATENIN, proliferative cells (KI67), and FIG. 3B, epithelial apical polarity (EZRIN) and tight junctions (ZO-1). DAPI, counterstain. "L" indicates HIO lumen. Bars, 100 µm. Images are representative of three independent experiments performed with 6 PEG-4MAL/Matrigel™ per condition (a,b).
Figure 3B:
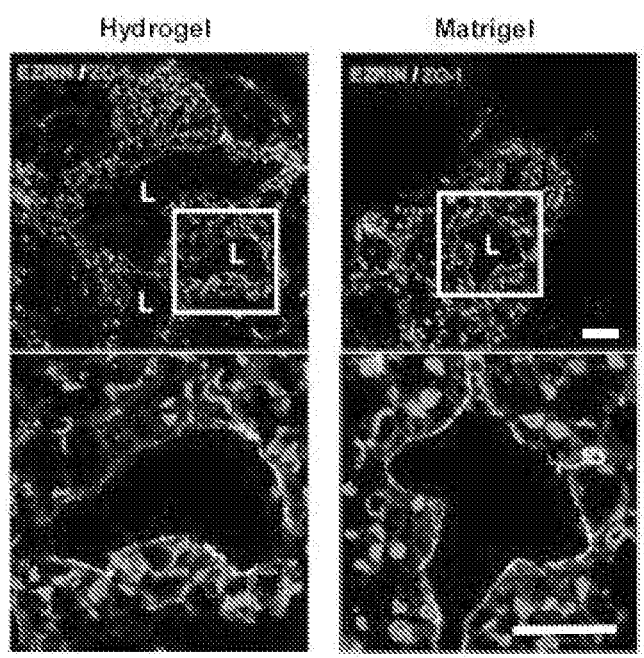
Figure 4:
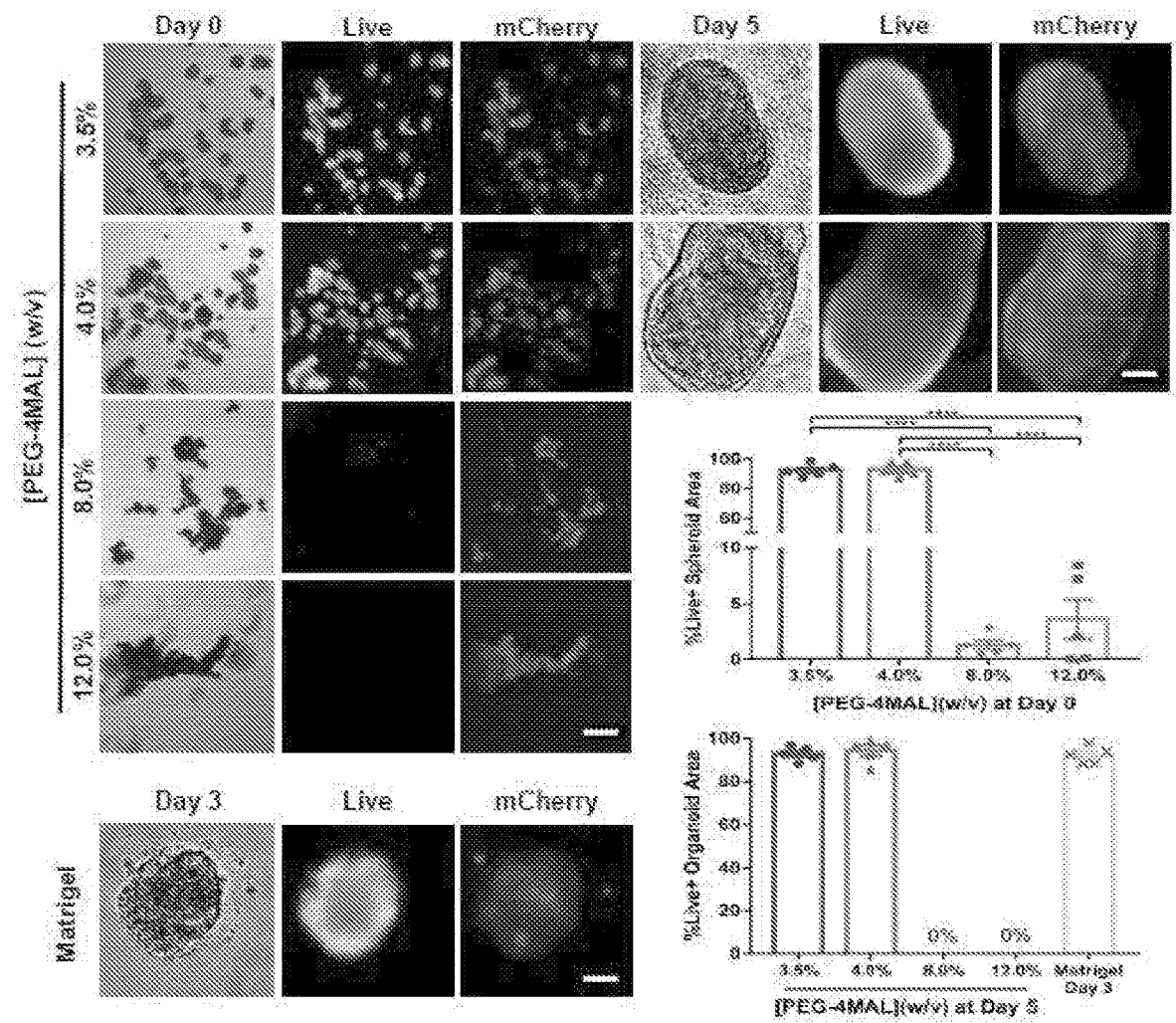
FIG. 4 depicts transmitted light and fluorescence microscopy images of mCherry-spheroids cultured in PEG-4MAL hydrogels of different polymer density or Matrigel™. Spheroids viability was assessed by Calcein-AM labeling at 2 hr after encapsulation (day 0) and at day 5 for PEG-4MAL conditions, and at day 3 for Matrigel™. Bar, 100 µm. Viability is quantified as percentage of total spheroid or organoid area stained for live or dead (mean±SEM; n=5 organoids analyzed per condition/time-point). One-way ANOVA with Tukey's multiple comparisons test showed significant differences between 3.5% or 4.0% PEG-4MAL and 8.0% or 12.0% PEG-4MAL at Day 0 ($****P<0.0001$). Graphs and images are representative of one and three independent experiments, respectively, performed with 6 PEG-4MAL/Matrigel™ per condition.
Figure 5A:
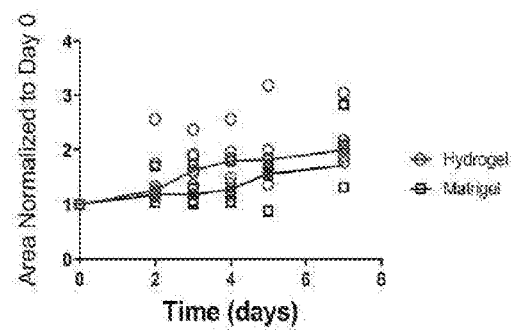
FIG. 5A depicts HIO projected area and FIG. 5B depicts feret diameter normalized to Day 0 values at different time-points after encapsulation in 4.0% PEG-4MAL-RGD hydrogel (●) or Matrigel™ (■) (n=6 or 4 organoids analyzed per condition/time-point). Repeated measures two-way ANOVA showed no significant difference between matrix types (P-value>0.05). Graph line represents the mean of the individual data points at each time-point.
Figure 5B:
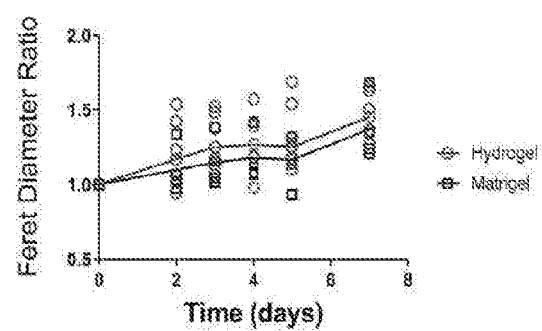
Figure 5C:
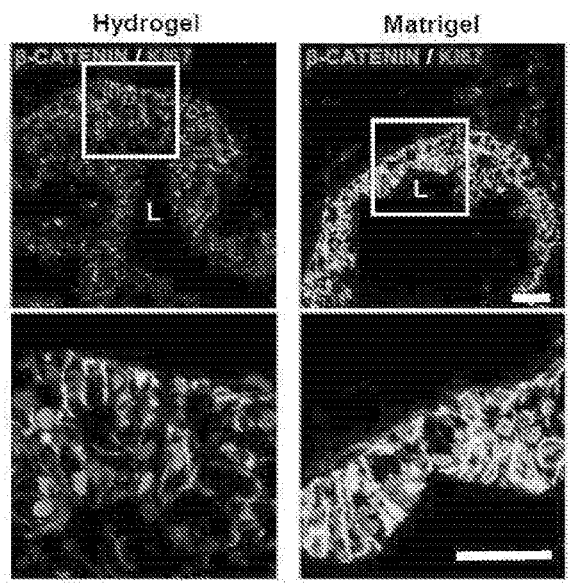
FIG. 5C and FIG. 5D Fluorescence microscopy images of a HIO at 21 d after encapsulation in 4.0% PEG-4MAL-RGD hydrogel or Matrigel™ and labeled for FIG. 5C β-CATENIN, proliferative cells (KI67), and FIG. 5D epithelial apical polarity (EZRIN) and tight junctions (ZO-1). DAPI, counterstain. "L" indicates HIO lumen. Bars, 100 μm. Graphs and images are representative of one and three independent experiments, respectively, performed with 6 PEG-4MAL/Matrigel™ per condition.
Figure 5D:
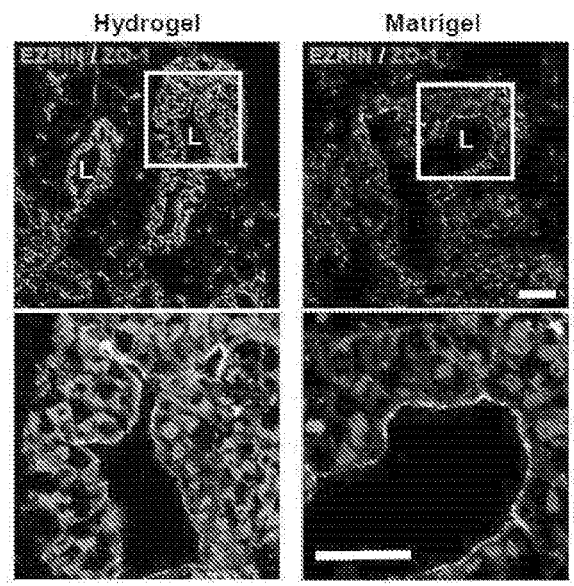
Figure 6A:
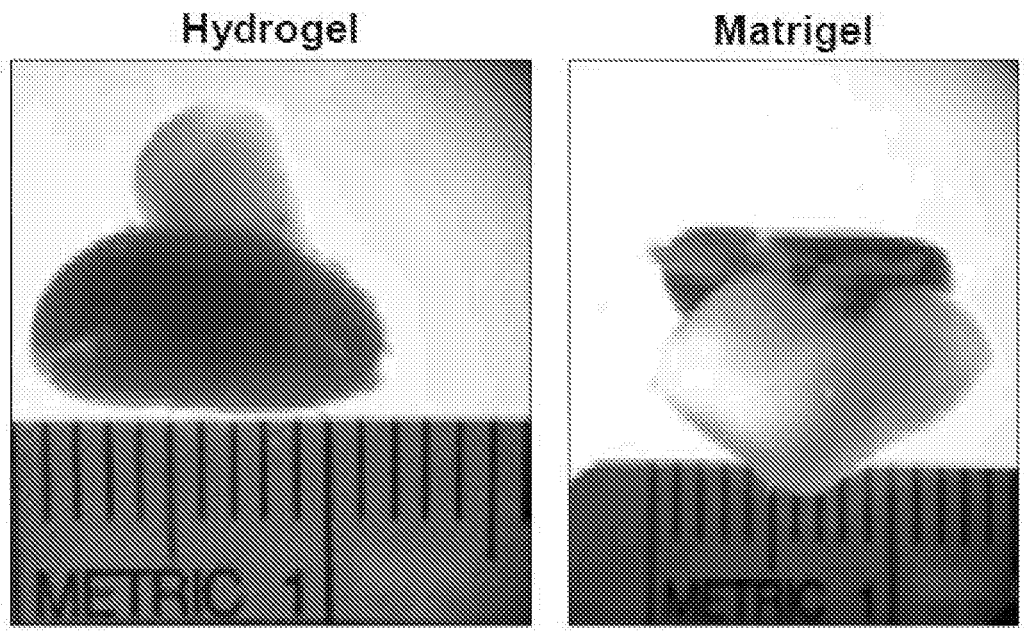
FIG. 6A depicts micrographs of dissected kidneys containing HIOs generated within PEG-4MAL-RGD or Matrigel™.
Figure 6B:
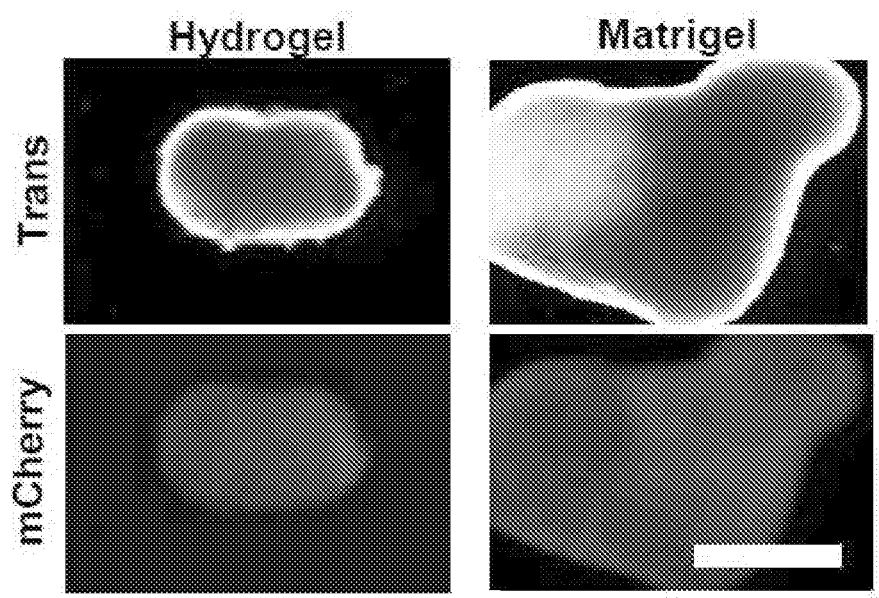
FIG. 6B depicts transmitted light and fluorescence microscopy (mCherry) images of harvested organoids. Bar, 0.5 cm.
Figure 6C:
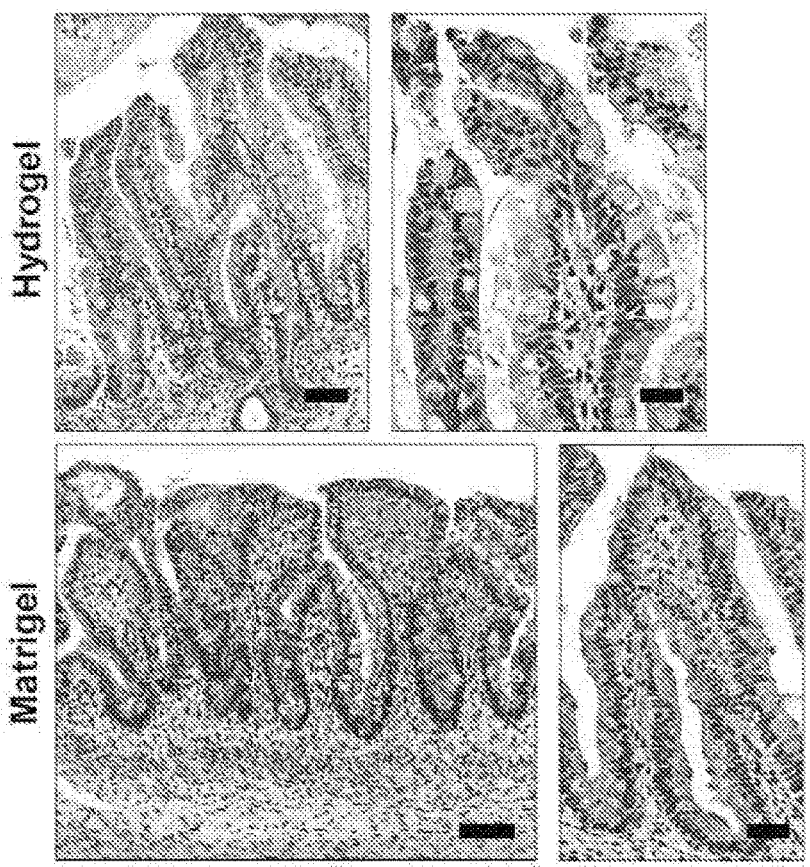
FIG. 6C depicts H&E staining demonstrates mature human intestinal crypt-villus structure.
Figure 6D:
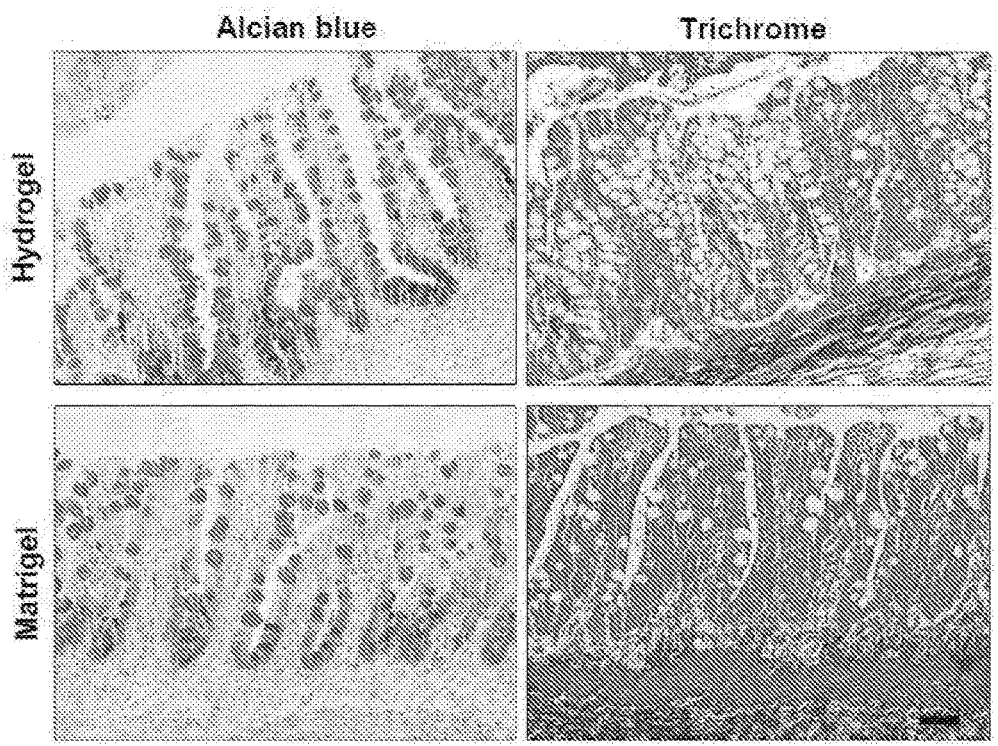
FIG. 6D depicts Alcian blue and trichrome staining reveal presence of differentiated goblet cells and organized collagen fibers. Bar, 100 μm.
Figure 6E:
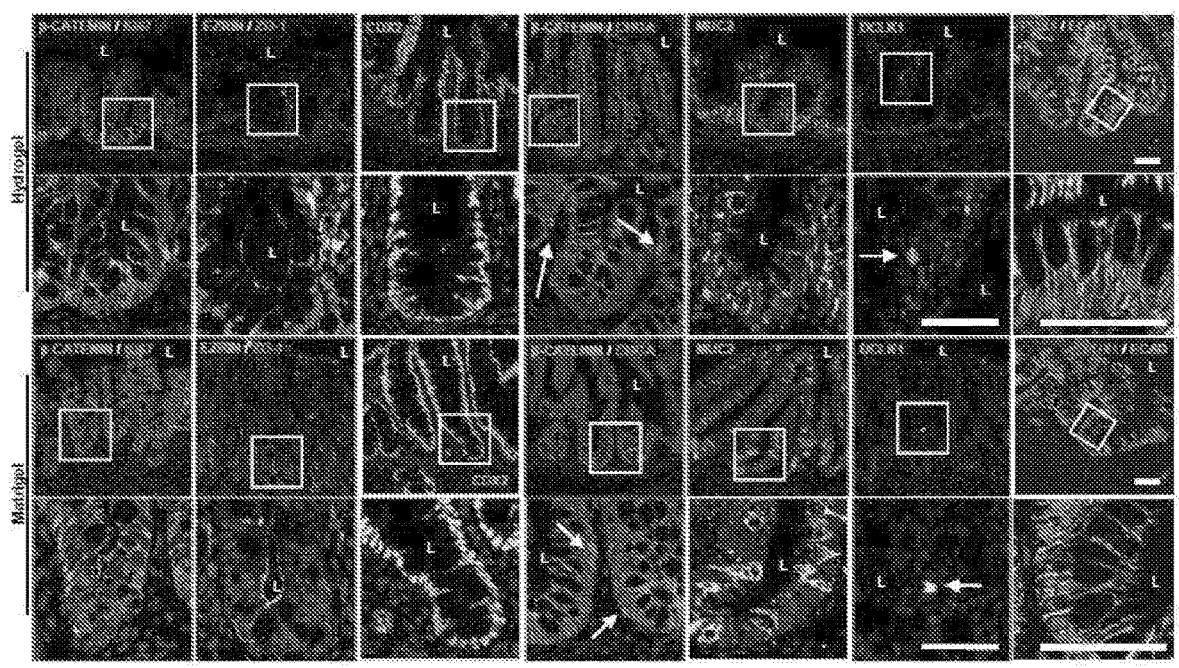
FIG. 6E depicts fluorescence microscopy images of HIOs labeled for (β-CATENIN, proliferative cells (KI67), epithelial apical polarity (EZRIN) and junctions (ZO-1 and ECAD), intestinal epithelial protein CDX2, enteroendocrine cells (CHGA), goblet cells (MUC2), tuft cells (DCLK1) and small intestinal marker (duodenum; PDX1). DAPI, counterstain. "L" indicates HIO lumen. White arrows show enteroendocrine cells or tuft cells. Bars, 50 μm. Images are representative of one experiment performed with 3 mice per condition.
Figure 7A:
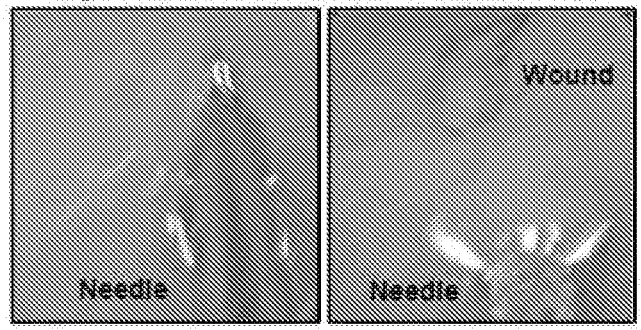
FIG. 7A depicts PEG-4MAL-generated HIOs mixed with engineered hydrogel precursor solutions were injected underneath mechanically-induced mucosal wounds, as seen through the colonoscope camera.
Figure 7B:
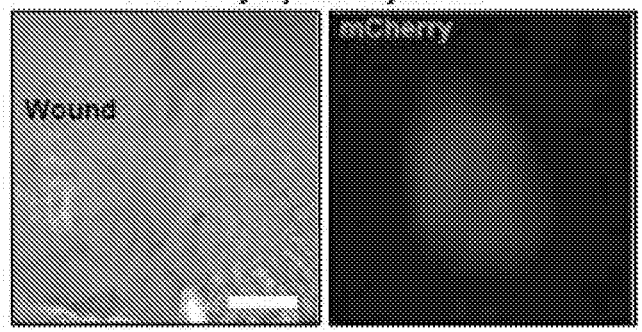
FIG. 7B depicts mechanically-induced mucosal wound and fluorescence imaging (mCherry) at the wound site at 5 d post-injection. Bar, 500 μm.
Figure 7C:
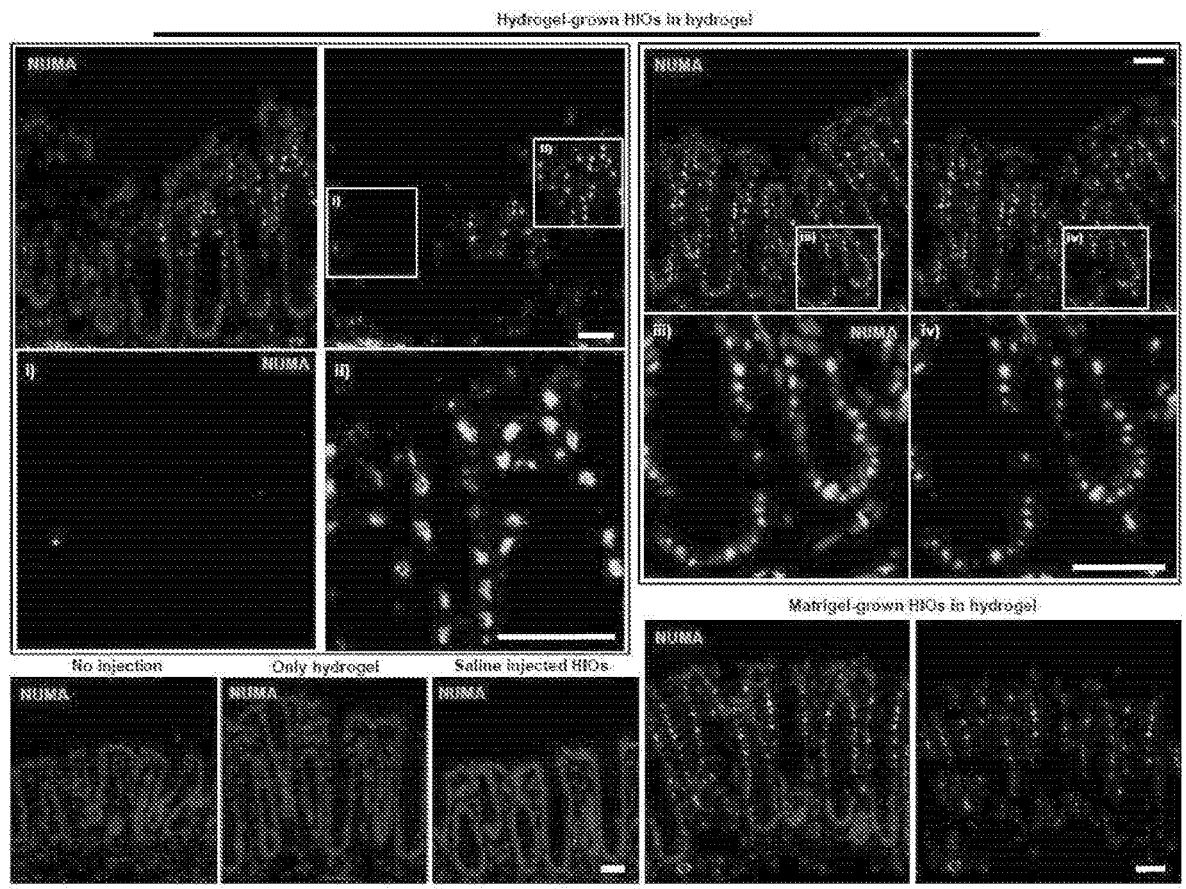
FIG. 7C depicts fluorescence microscopy images of murine colonic tissue at the wound site labeled for human cell nuclei (NUMA) at 4 weeks post-delivery. Left: Images from wound edge showing insets from i) adjacent host tissue and ii) wound. Right: Images from wound center showing insets at wound site. DAPI, counterstain. Bars, 100 μm.
Figure 7D:
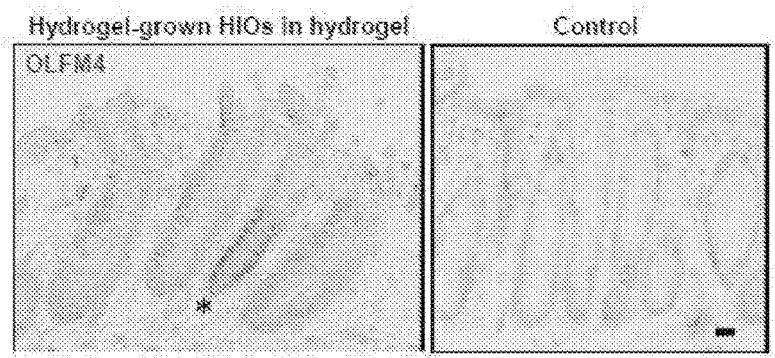
FIG. 7D depicts In situ hybridization, stained for human OLFM4+ cells. Bar, 50 μm. Images are representative of two experiment performed with 4 mice per condition (five colonic wounds/injections per mouse; a-d).
Figure 8:
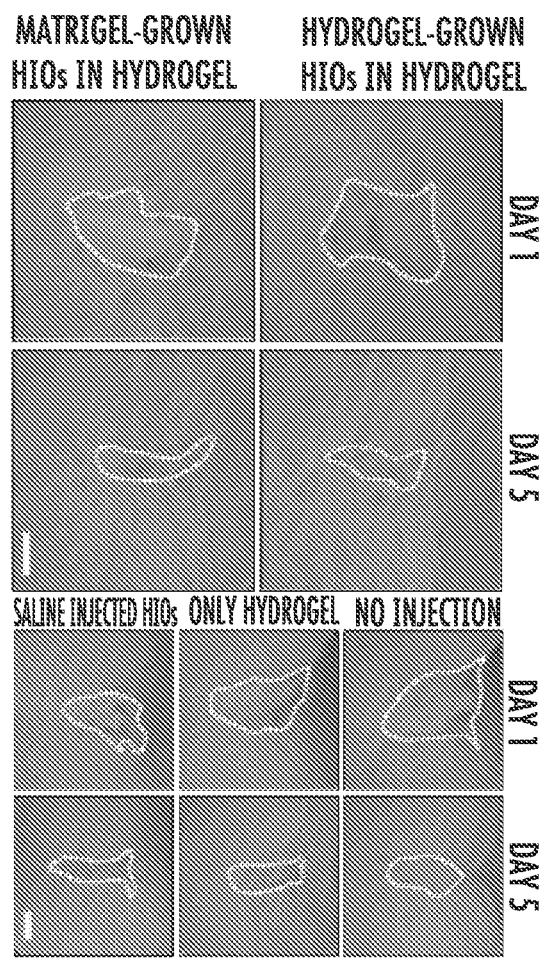
FIG. 8 depicts images of mucosal wounds at 1 d (prior to injection) or 5 d post-injury in murine colon as seen through the colonoscope camera. Mucosal wound area at 5 d post-injury was normalized to day 1 (prior to injection) values (mean±SEM). Five colonic wounds per mouse were analyzed and averaged (n=4 mice per condition). One-way ANOVA with Tukey's multiple comparisons test showed significant difference between Hydrogel-grown HIOs in hydrogel (●) or Matrigel-grown HIOs in hydrogel (■) and Saline injected HIOs (▲) Only hydrogel (♦) or No injection group (X) (P<0.01, *P<0.001, ****P<0.0001). Bars, 500 μm. Images and graph are representative of one experiment performed with 4 mice per condition (five colonic wounds/injections per mouse; a-e). Source data are available in Supplementary Table 1.
Figure 8:
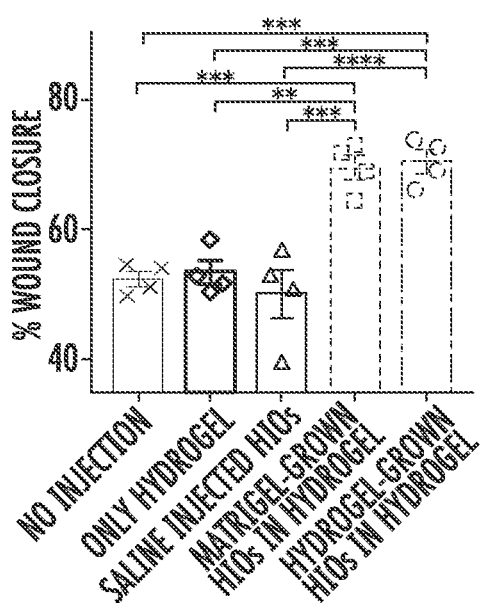
Figure 9A:
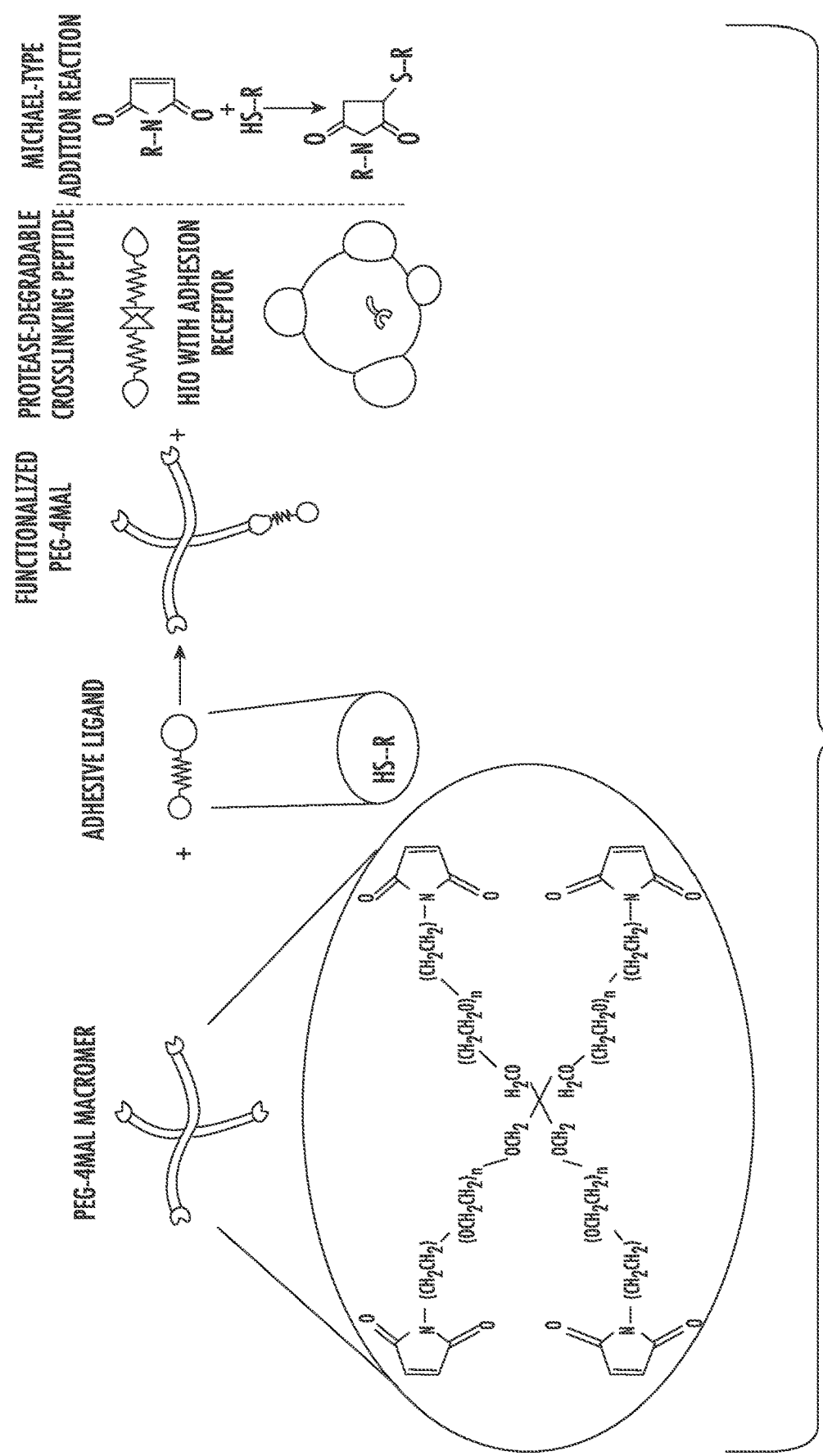
FIG. 9A depicts PEG-4MAL macromers are conjugated with thiol-containing adhesive peptide to produce a functionalized PEG-4MAL macromer, which is then crosslinked in the presence of HIOs using protease-cleavable peptides containing terminal cysteines to form a FIG. 9B hydrogel network.
Figure 9B:
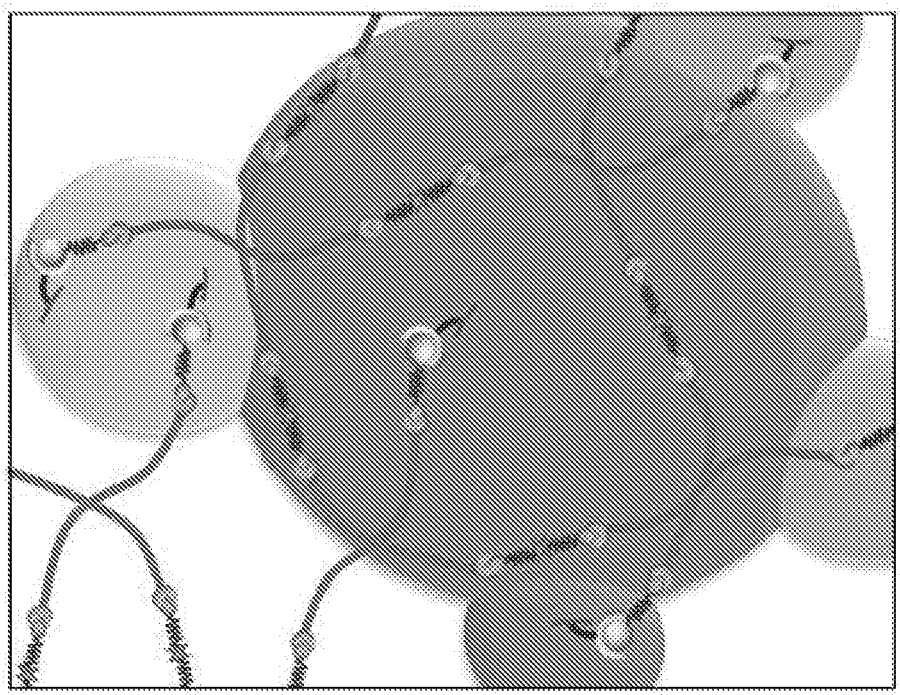
FIG. 9C and FIG. 9D depict the relationship between polymer density (wt %) and storage modulus (FIG. 9C) or loss modulus (FIG. 9D) (mean±SEM; n=10 independently prepared hydrogels per condition).
FIG. 9E depicts schematic of spheroid development into HIOs within Matrigel™ and further growth within PEG-4MAL hydrogel.
FIG. 9F depicts schematic of spheroid development into HIOs within hydrogel. (c,d) Graphs are representative of one experiment. Source data are available in Supplementary Table 1.
Figure 9C:
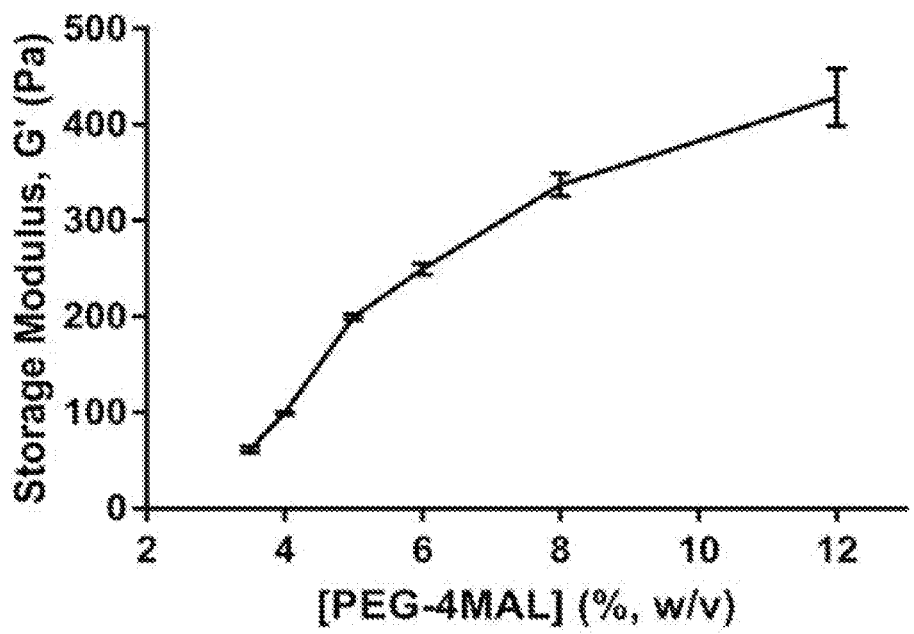
Figure 9D:
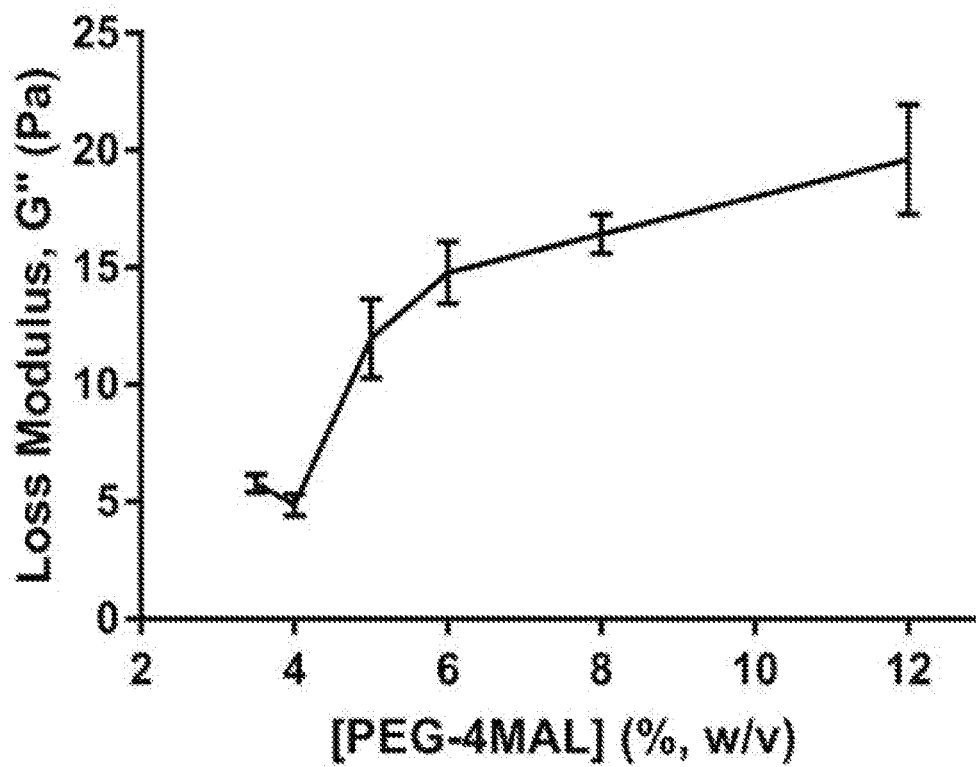
Figure 9E:
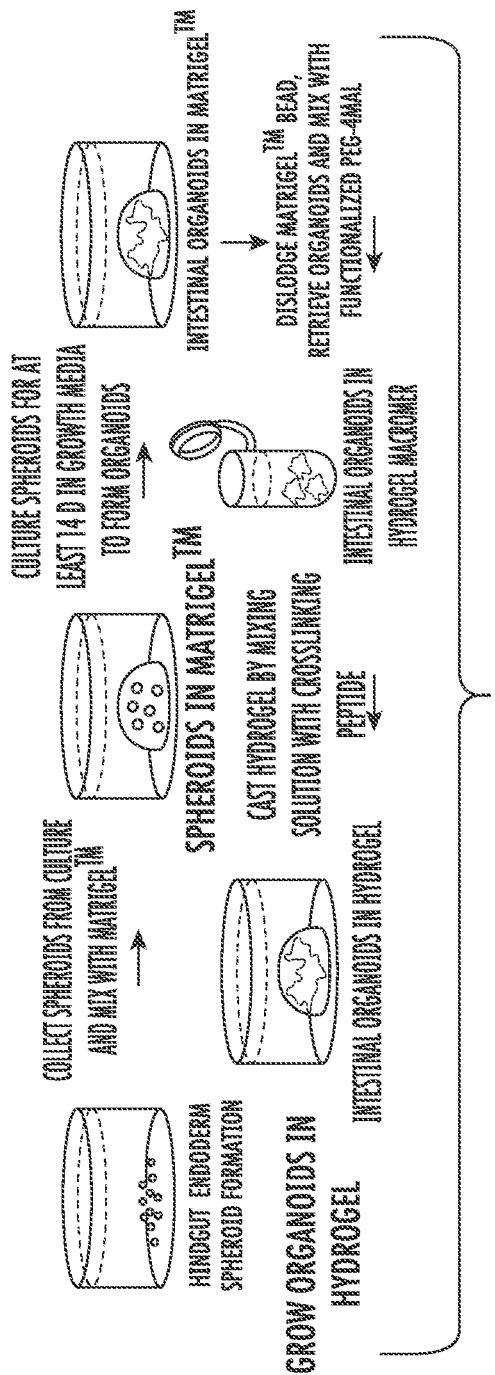
Figure 9F:
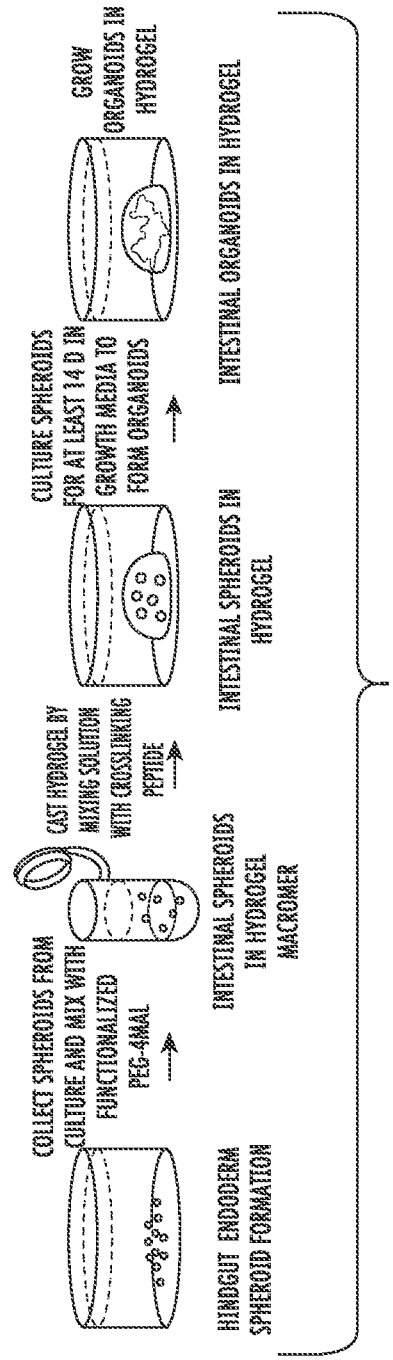
Figure 10A:
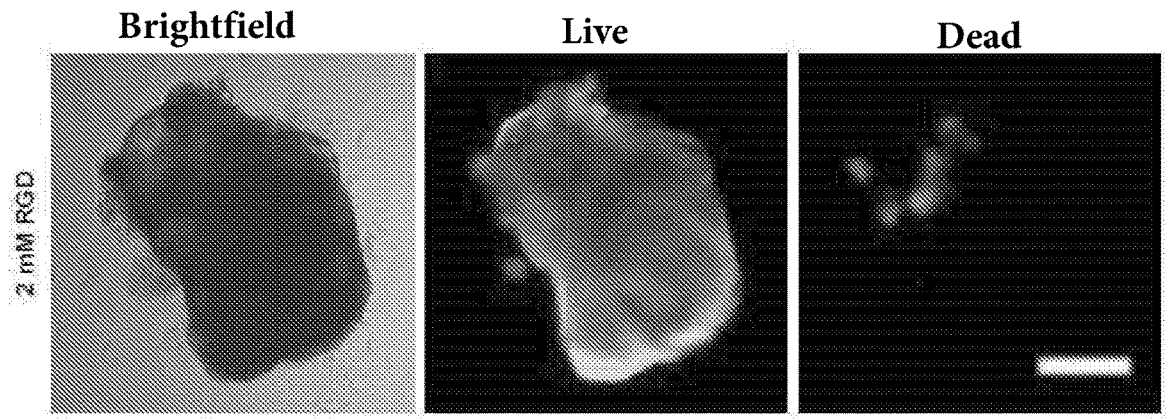
FIG. 10 depicts transmitted light and fluorescence microscopy images of HIOs cultured in 4.0% PEG-4MAL hydrogels functionalized with RGD (FIG. 10A), inactive scrambled RDG peptide (FIG. 10B), or non-degradable crosslinker (DTT) (FIG. 10C). HIO viability was assessed at 7 d after encapsulation.
FIG. 10D and FIG. 10E depict transmitted light microscopy images of Matrigel™-generated HIOs cultured within 4.0% PEG-4MAL-RGD hydrogel (FIG. 10D) or Matrigel™ over time (FIG. 10E). Bars, 500 μm. Images are representative of three different experiments performed with (a-c) 4 or (d,e) 12 PEG-4MAL/Matrigel™ per condition.
Figure 10B:
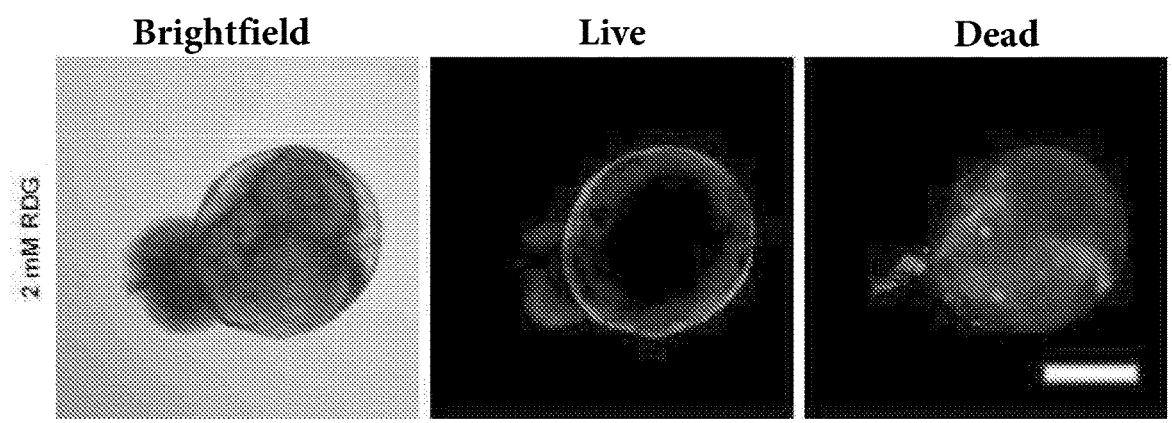
Figure 10C:
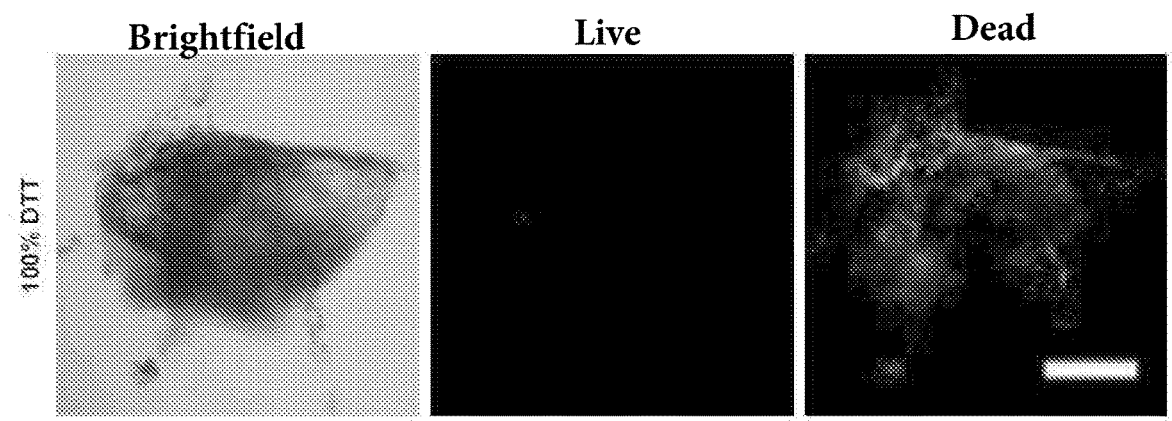
Figure 10D:
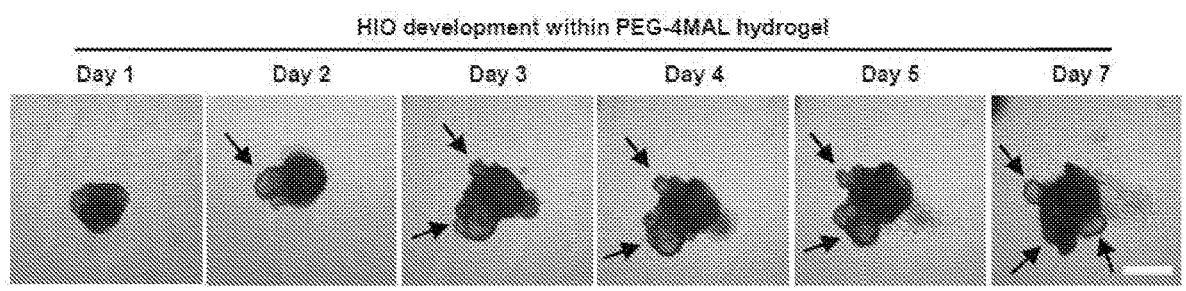
Figure 10E:
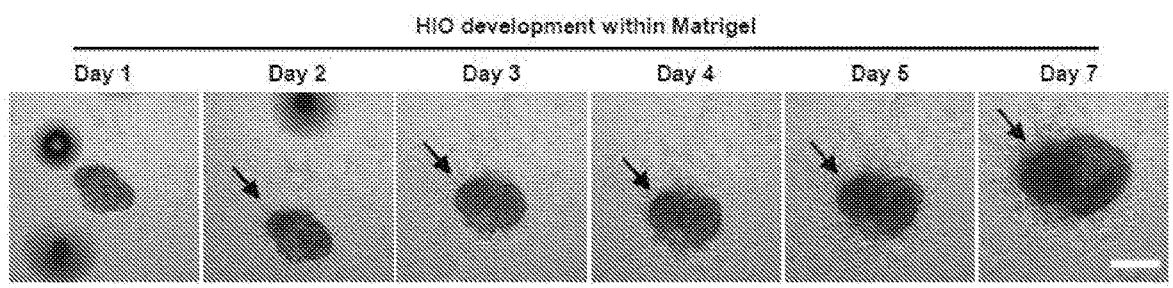
Figure 11A:
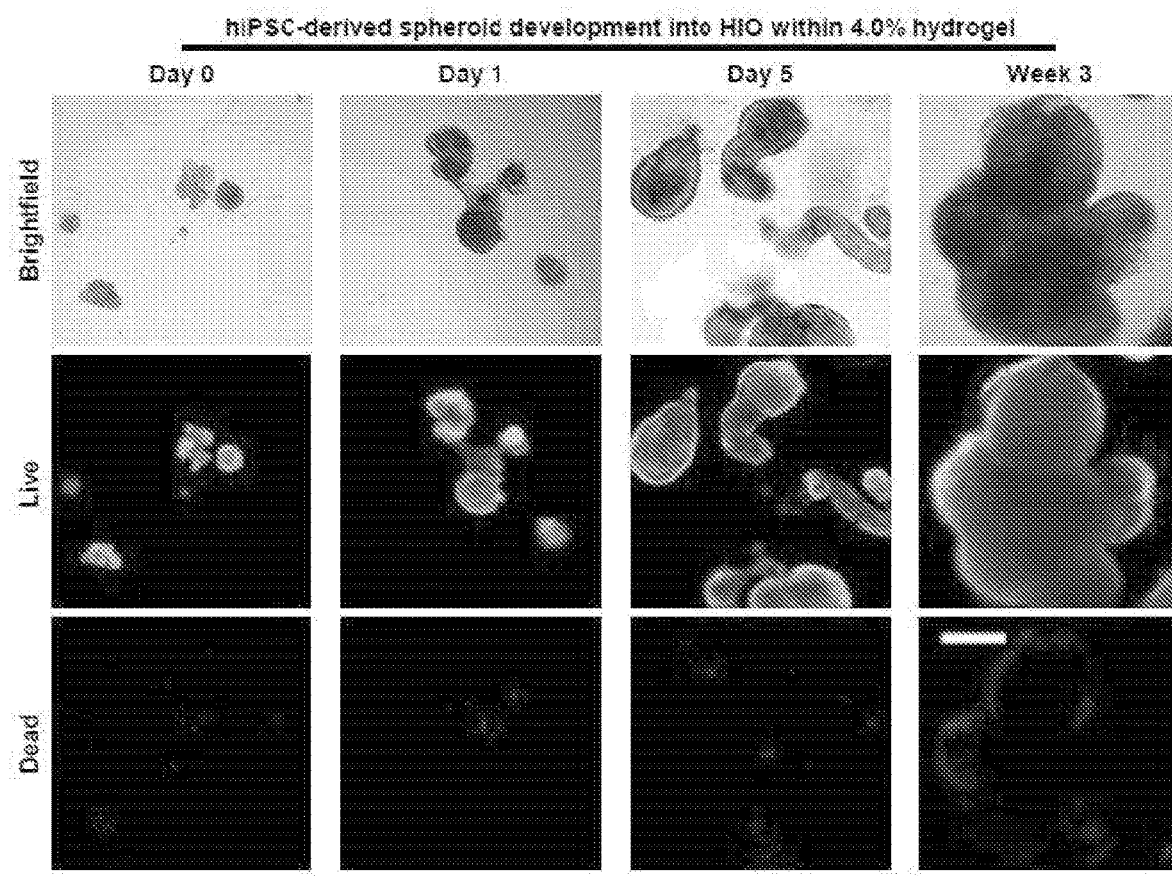
FIG. 11 depicts transmitted light and fluorescence microscopy images of hiPSC-derived HIO generation within 4.0% PEG-4MAL-RGD hydrogels (FIG. 11A), Matrigel™ (FIG. 11B), or 8.0% PEG-4MAL-RGD hydrogels (FIG. 11C), hiPSC-derived spheroid and HIO viability was assessed at different time-points after encapsulation.
FIG. 11D depicts transmitted light microscopy images of hESC-derived HIO generation within 4.0% PEG-4MAL-RGD hydrogels. These organoids were never encapsulated within Matrigel™. Black arrows show epithelial budding. Bars, 500 μm. Images are representative of three different experiments performed with 12 PEG-4MAL/Matrigel™ per condition (a-c).
Figure 11B:
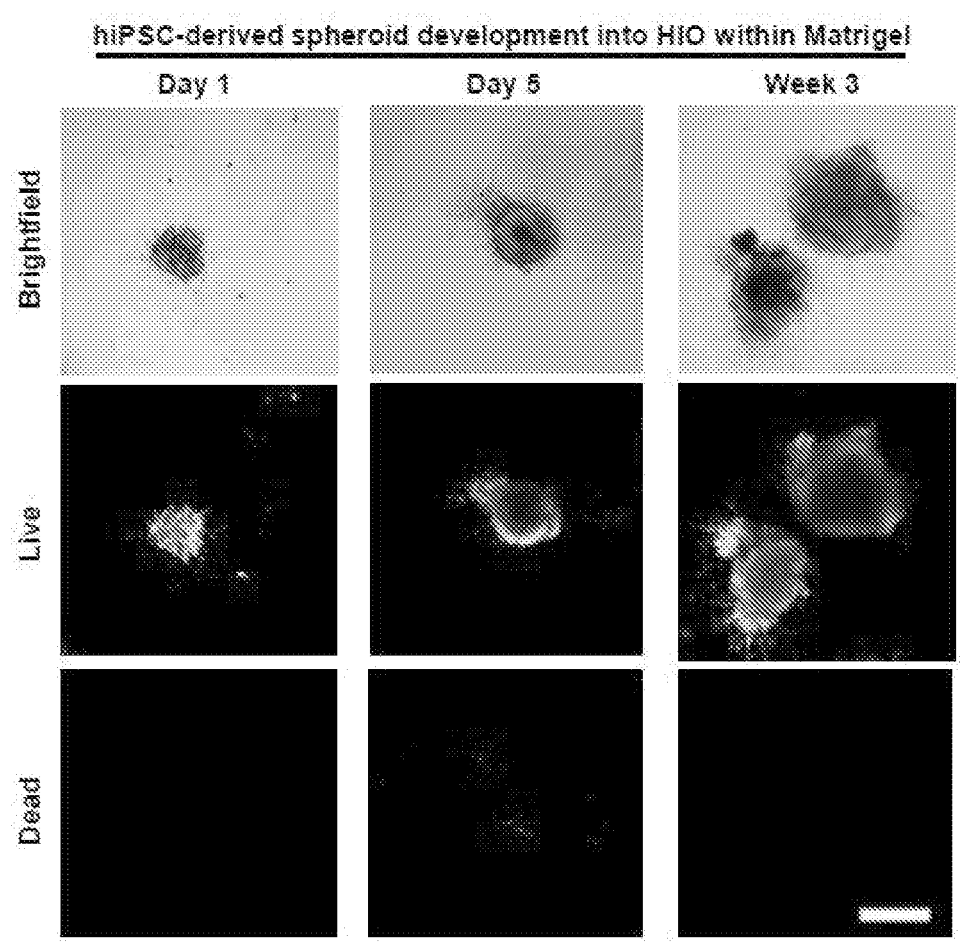
Figure 11C:
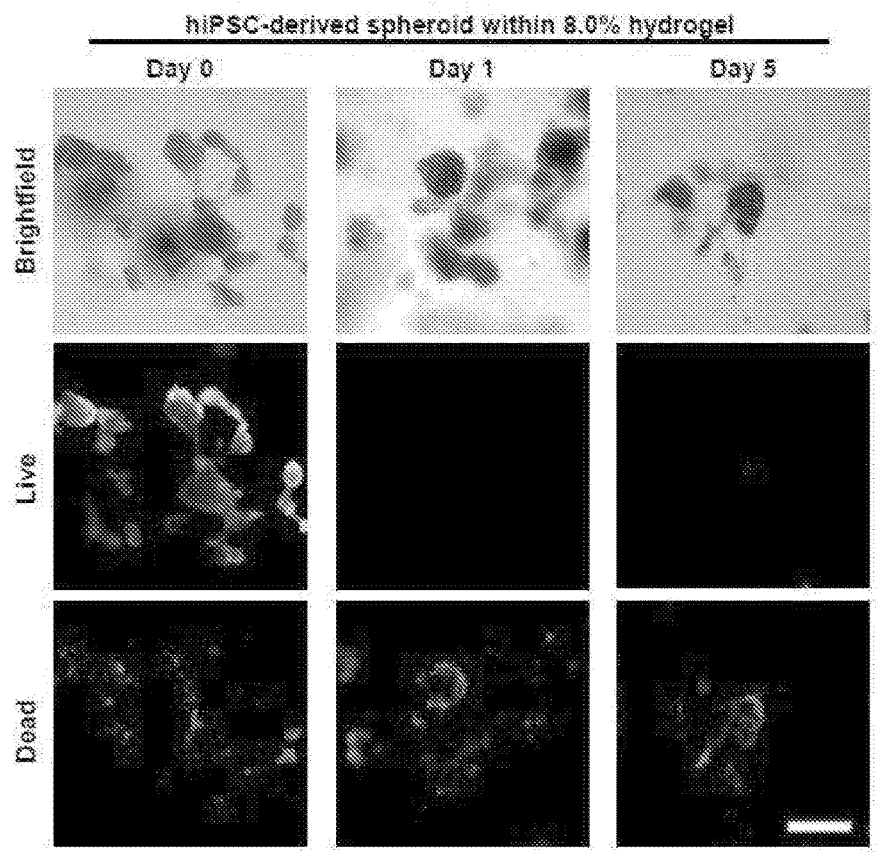
Figure 11D:
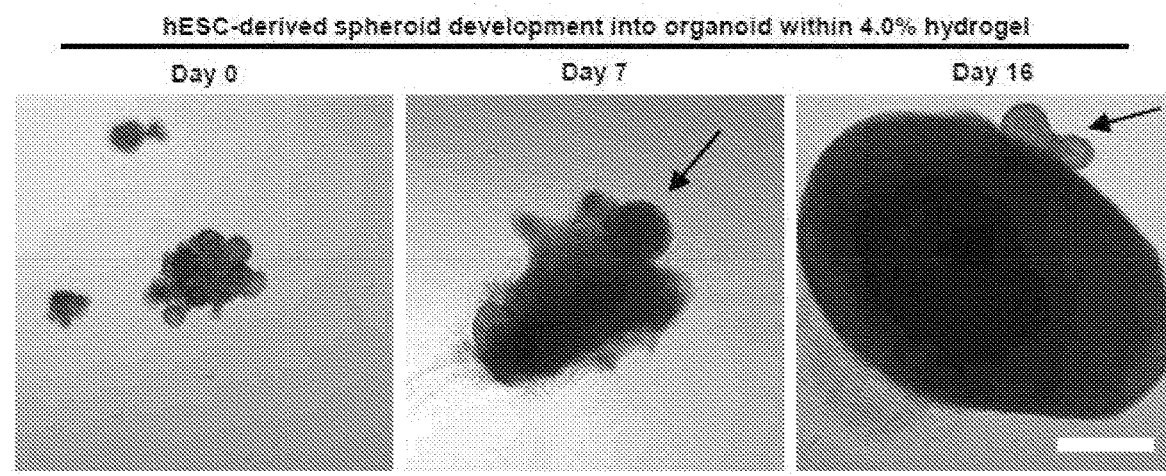
Figure 12A:
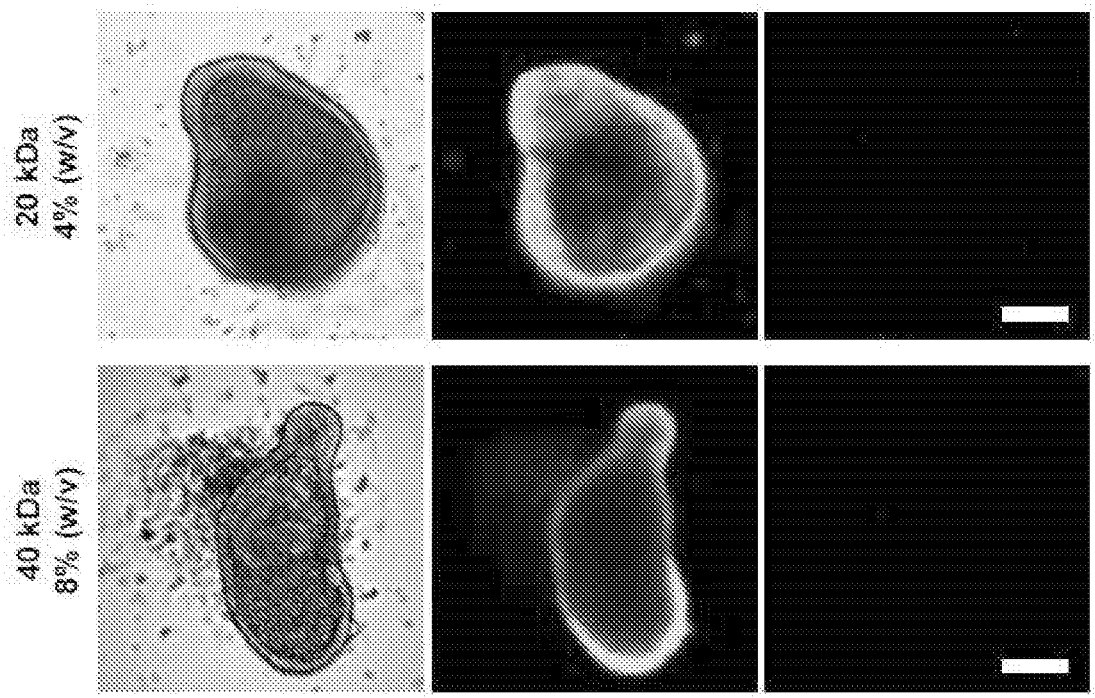
FIG. 12A depicts transmitted light and fluorescence microscopy images of HIO generation within 20 kDa (4.0%) or 40 kDa (8.0%) PEG-4MAL-RGD hydrogels. HIO viability was assessed at 5 d after encapsulation.
Figure 12B:
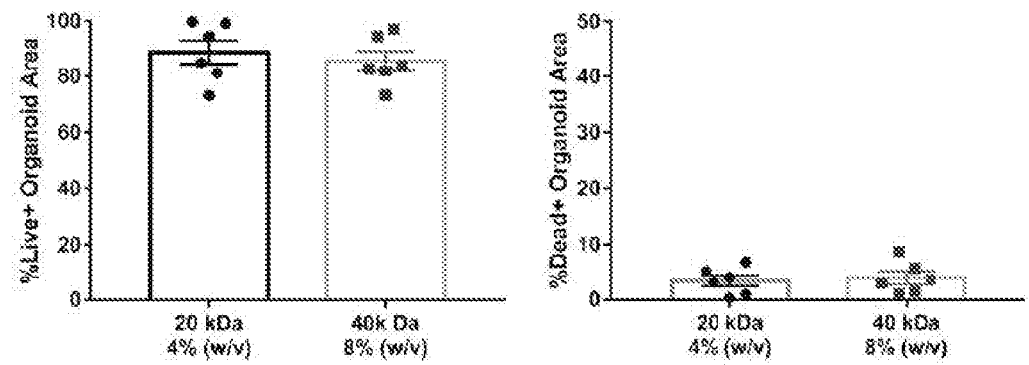
FIG. 12B depicts percentage of total organoid area stained for live or dead (mean±SEM) after 5 d of encapsulation (n=6 organoids analyzed per condition).
Figure 12C:
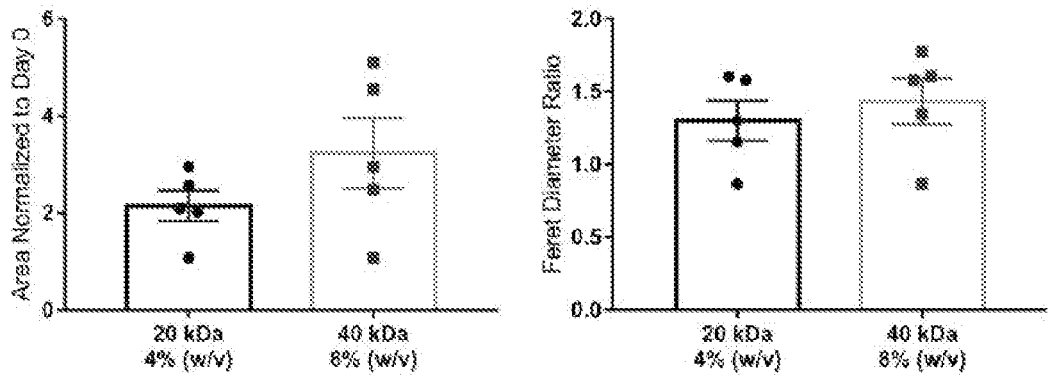
FIG. 12C depicts HIO projected area and Feret diameter normalized to Day 0 values (mean±SEM) after 5 d of encapsulation (n=5 organoids analyzed per condition). Unpaired two-tailed t-test with Welch's correction showed no significant differences between HIO viability or HIO size parameters within 20 kDa (4.0%) and 40 kDa (8.0%) PEG-4MAL-RGD (P-value>0.05).
Figure 12D:
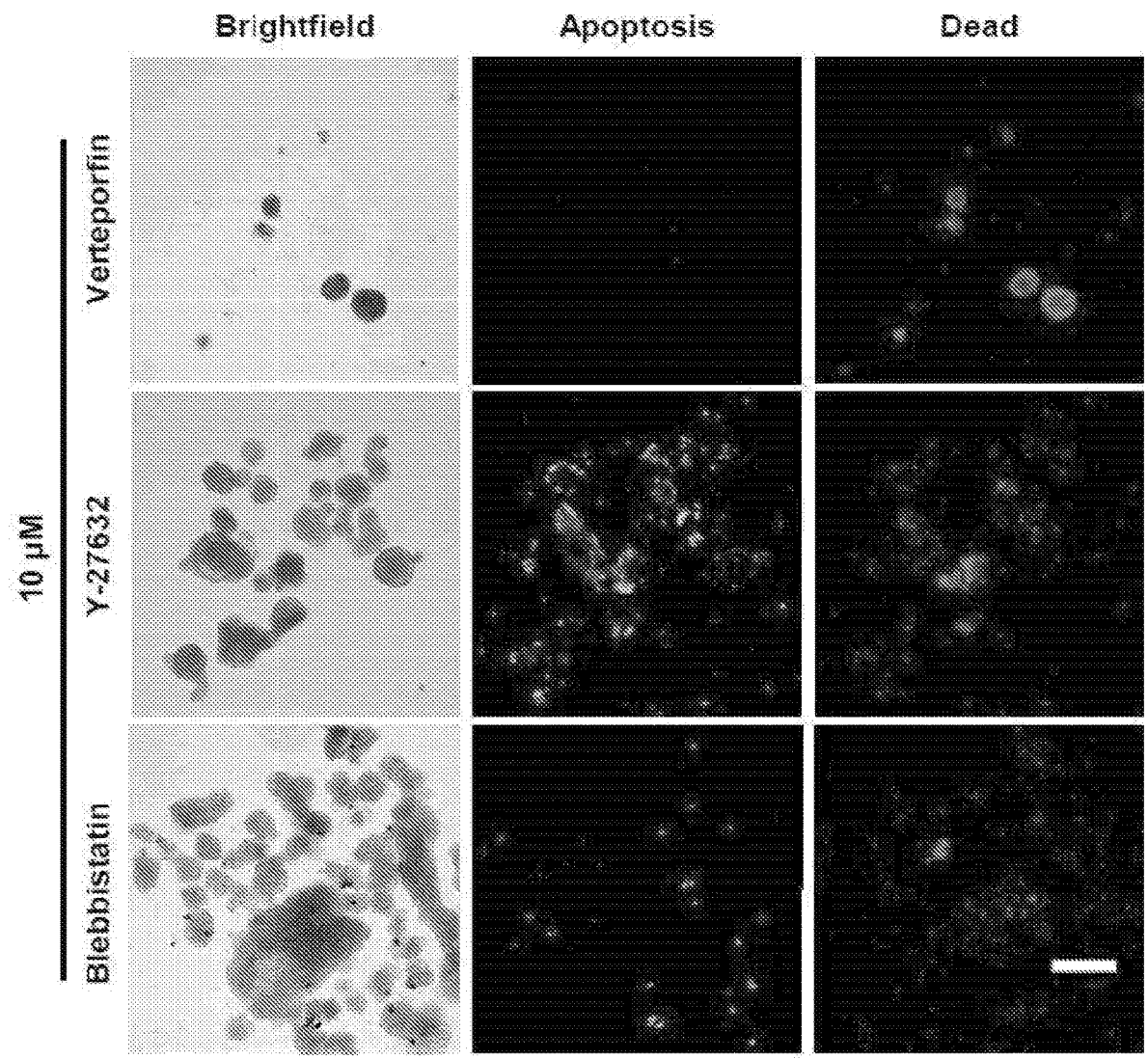
FIG. 12D and FIG. 12E depict transmitted light and fluorescence microscopy images of spheroids cultured within 4.0% PEG-4MAL-RGD hydrogels supplemented with 10 μM (FIG. 12D) or 30 μM of verteporfin, Y-27632 or blebbistatin FIG. 12E), or DMSO (vehicle control) (FIG. 12F). Spheroids death was assessed by annexin-V (apoptosis) and propidium iodide (dead) labeling at 1 d after encapsulation. Bars, 100 μm. Data is representative of one experiment performed with 12 PEG-4MAL hydrogels per condition.
Figure 12E:
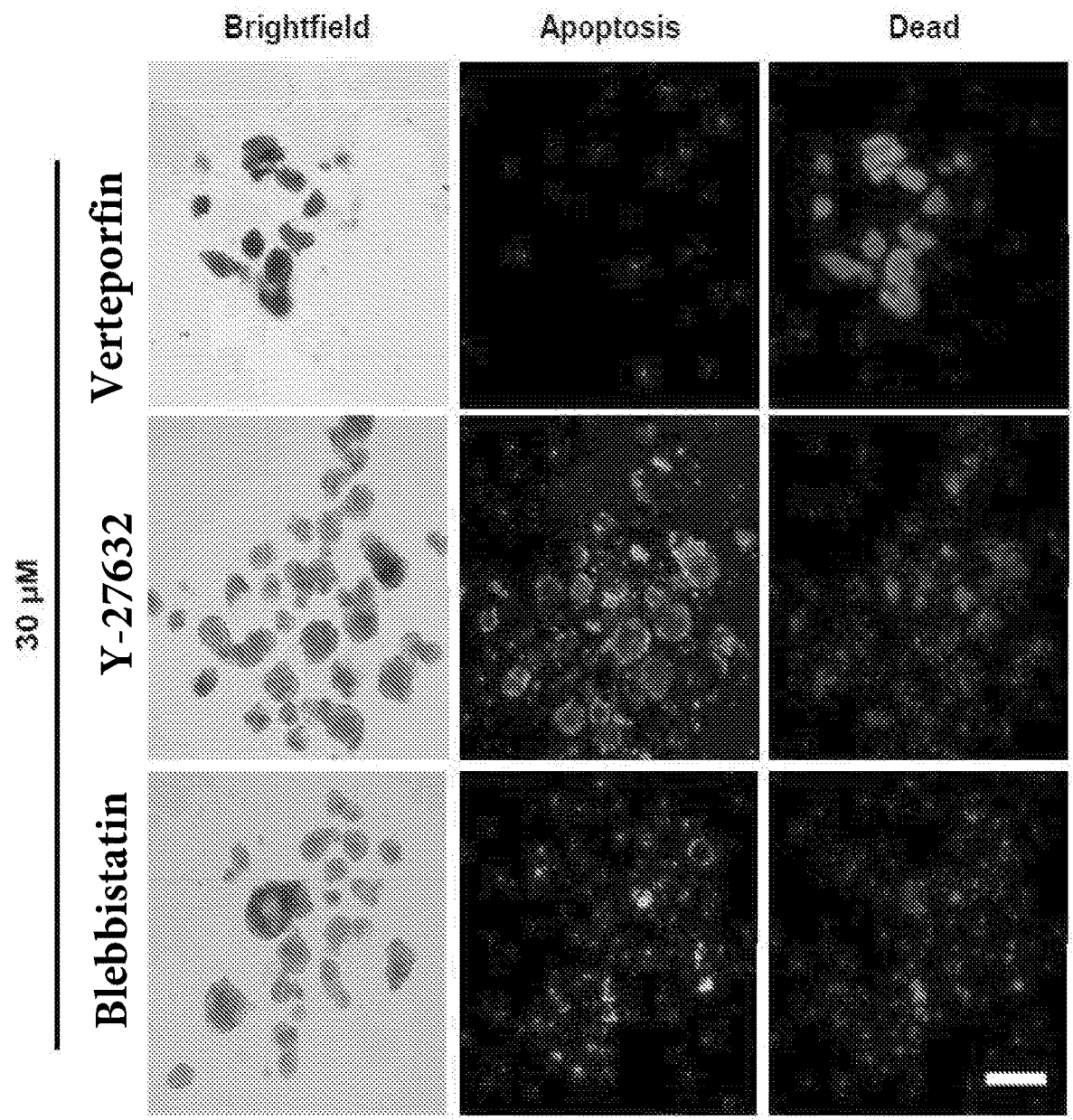
Figure 12F:
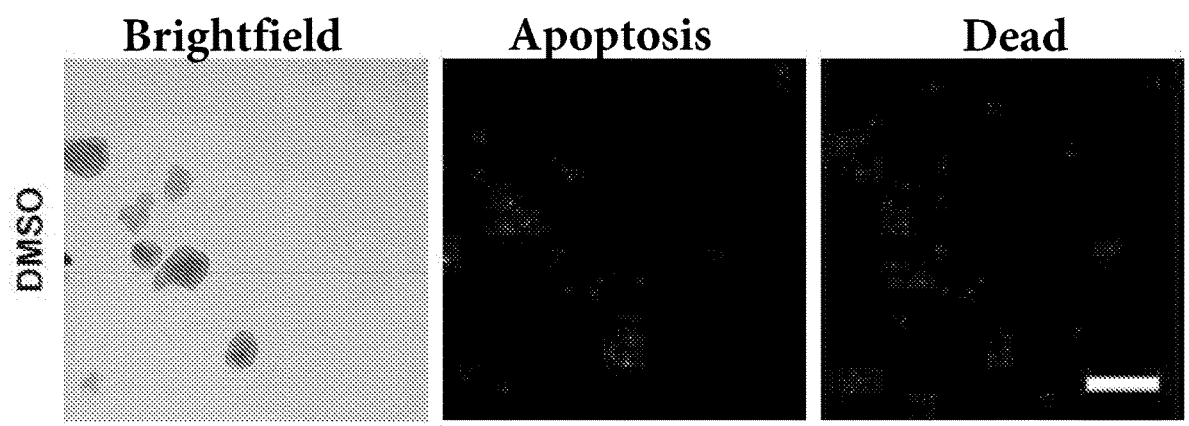
Figure 13:
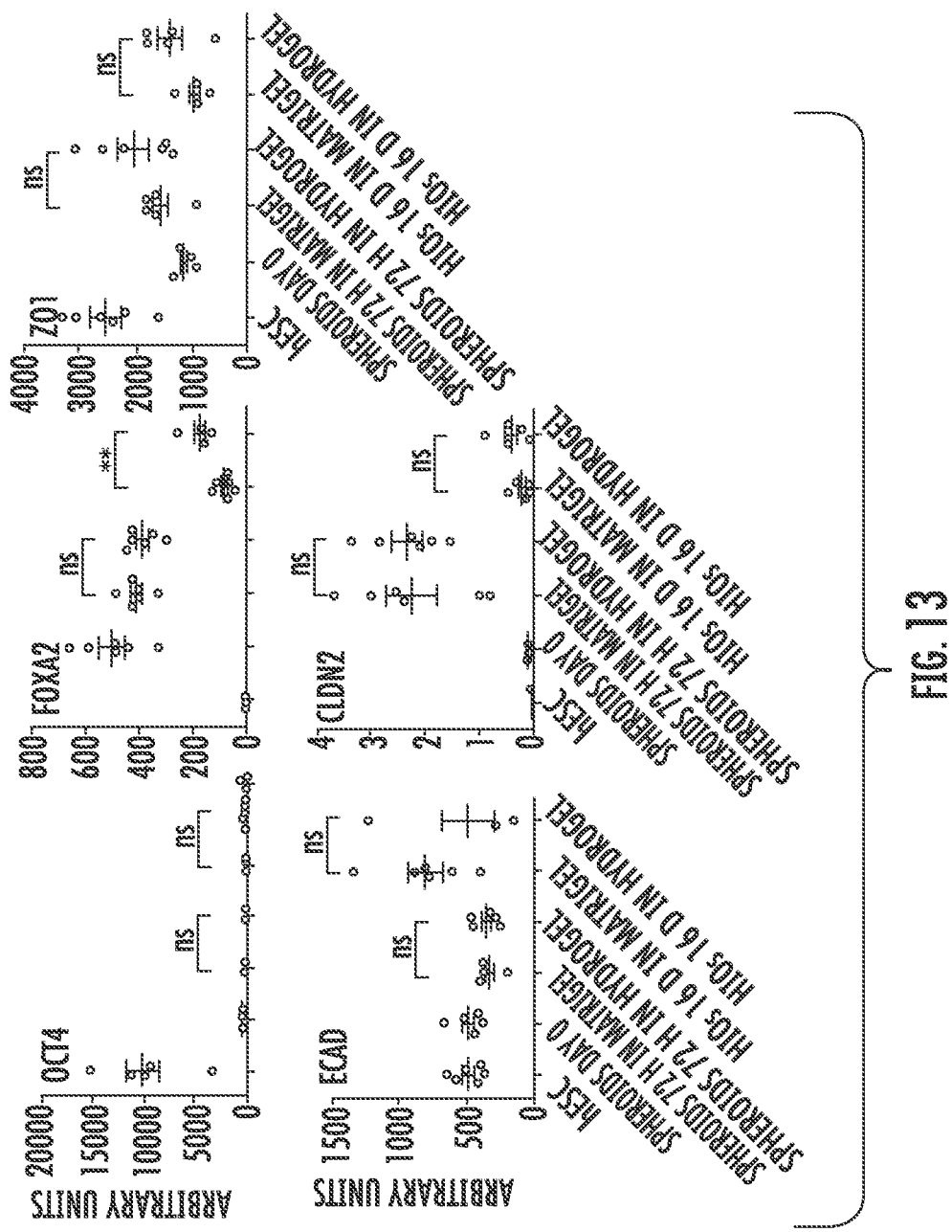
FIG. 13 depicts RNA levels of pluripotency (OCT4), endoderm (FOXA2), and epithelial junction (ZO1, ECAD and CLDN2) genes, as quantified by RT-qPCR (mean±SEM; n=6 samples per condition). Unpaired two-tailed t-test was used to identify statistical differences between matrix types (**P<0.01; ns, not significant). The results are representative of one experiment.
Figure 14A:
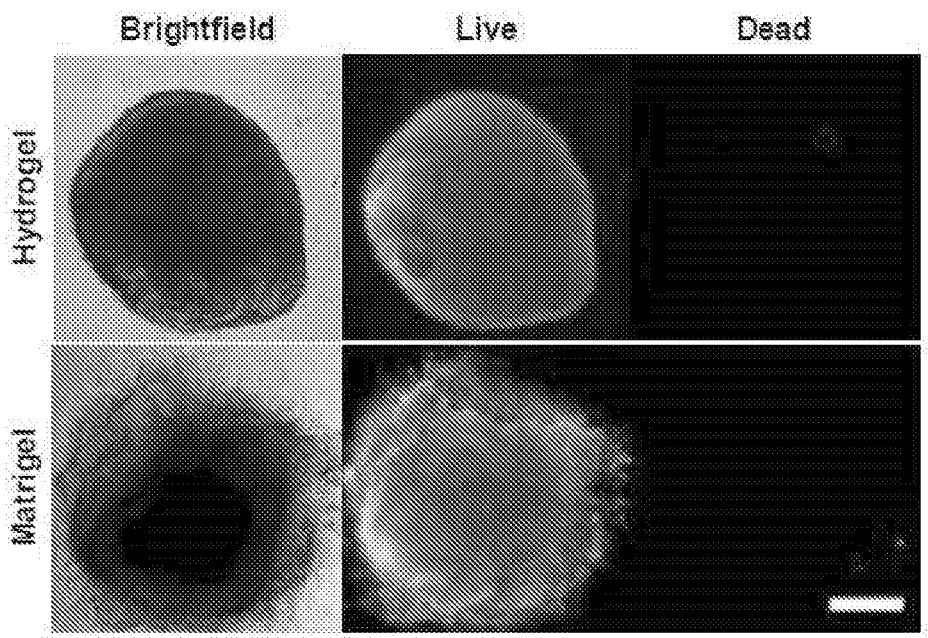
FIG. 14A depicts transmitted light and fluorescence microscopy images of HIOs cultured in 4.0% PEG-4MAL-RGD hydrogels or Matrigel™. HIO viability was assessed at 7 d after encapsulation. Bar, 500 μm.
Figure 14B:
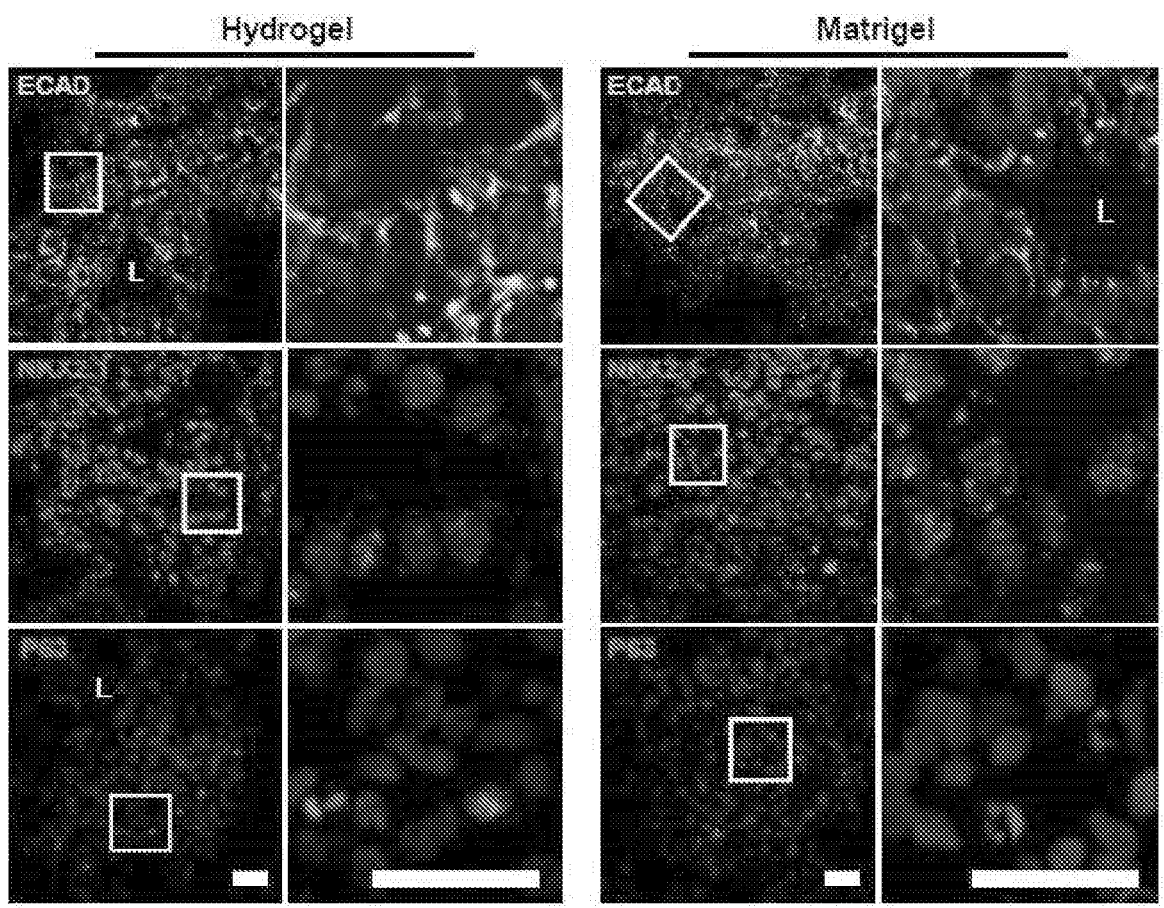
FIG. 14B depicts fluorescence microscopy images of HLO at 7 d after encapsulation in 4.0% PEG-4MAL-RGD hydrogel or Matrigel™ and labeled for e-cadherin (ECAD), lung epithelia (NKX2.1), and basal cells (P63). DAPI, counterstain. "L" indicates HLO lumen. Bars, 25 μm. The results are representative of one experiment performed with 6 PEG-4MAL/Matrigel™ per condition.
Figure 15A:
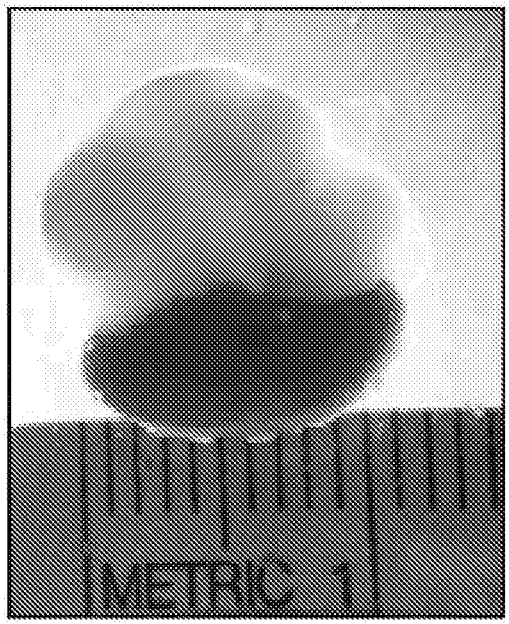
FIG. 15A depicts micrographs of dissected kidney containing HIOs.
Figure 15B:
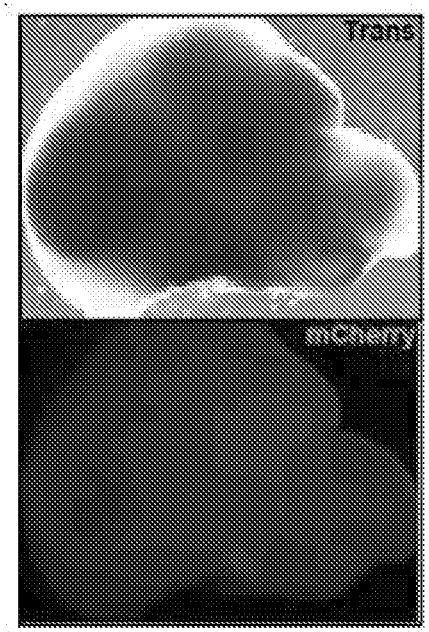
FIG. 15B depicts transmitted light and fluorescence microscopy (mCherry) images of harvested HIOs.
Figure 15C:
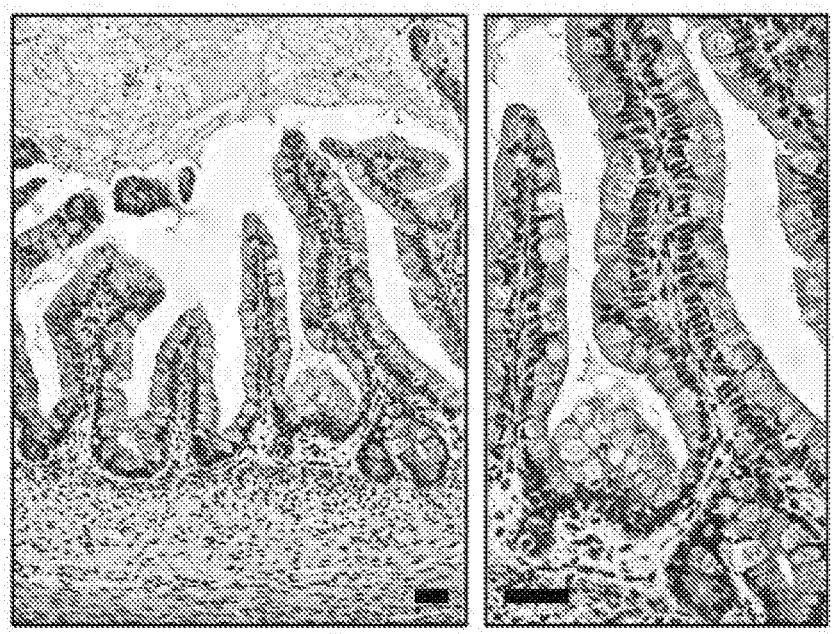
FIG. 15C depicts H&E staining demonstrates mature human intestinal crypt-villus structure.
Figure 15D:
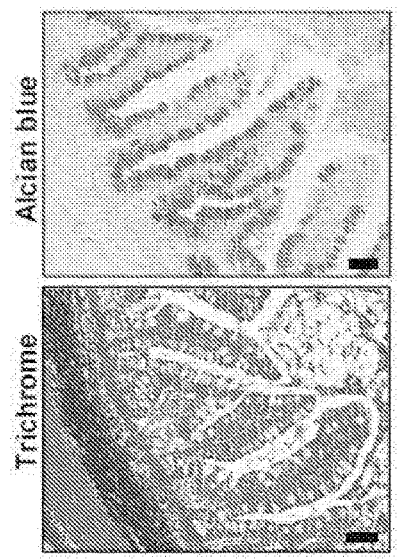
FIG. 15D depicts Alcian blue and trichrome staining show the presence of differentiated goblet cells and organized collagen fibers. Bar, 100 μm.
Figure 15E:
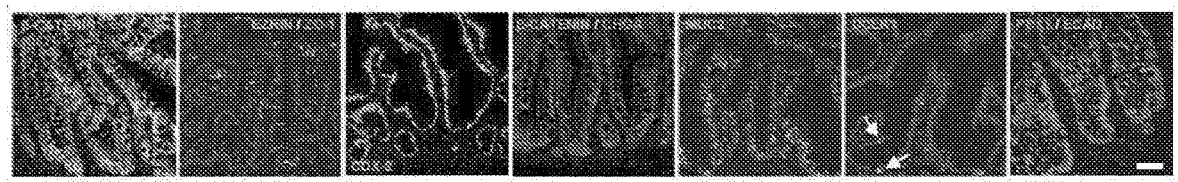
FIG. 15E depicts fluorescence microscopy images of harvested HIOs labeled for β-CATENIN, proliferative cells (KI67), epithelial apical polarity (EZRIN) and junctions (ZO-1 and ECAD), intestinal epithelial protein CDX2, enteroendocrine cells (CHGA), goblet cells (MUC2), tuft cells (DCLK1) and small intestinal marker (duodenum; PDX1). DAPI, counterstain. White arrows show tuft cells. Bar, 50 μm.
Figure 16A:
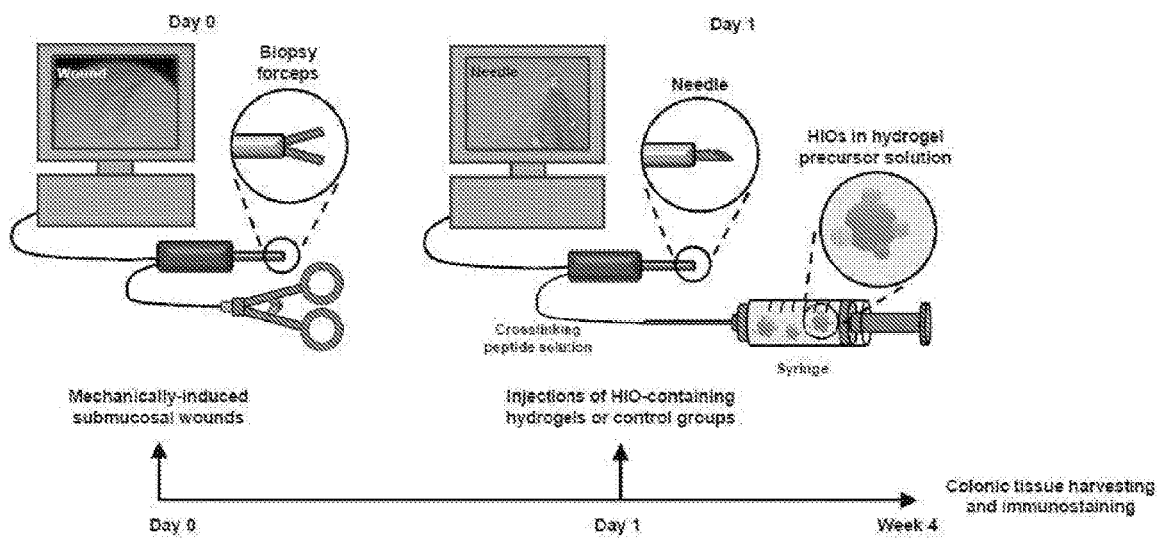
FIG. 16A depicts mechanically-induced submucosal wounds were performed in the distal colon of mice using a mechanical probe through a mouse colonoscope. One day post-wounding HIOs generated in engineered 4% PEG-4MAL-RGD hydrogels or Matrigel™ were recovered from the matrix, mixed with the engineered hydrogel precursor solutions, and injected underneath the submucosal wounds. A group with no injections, HIOs injected in saline, or injection of HIO-free hydrogel precursor solutions were used as control groups. Distal colon tissue harvest, immunostaining and imaging was performed 4 weeks post-wounding.
Figure 16B:
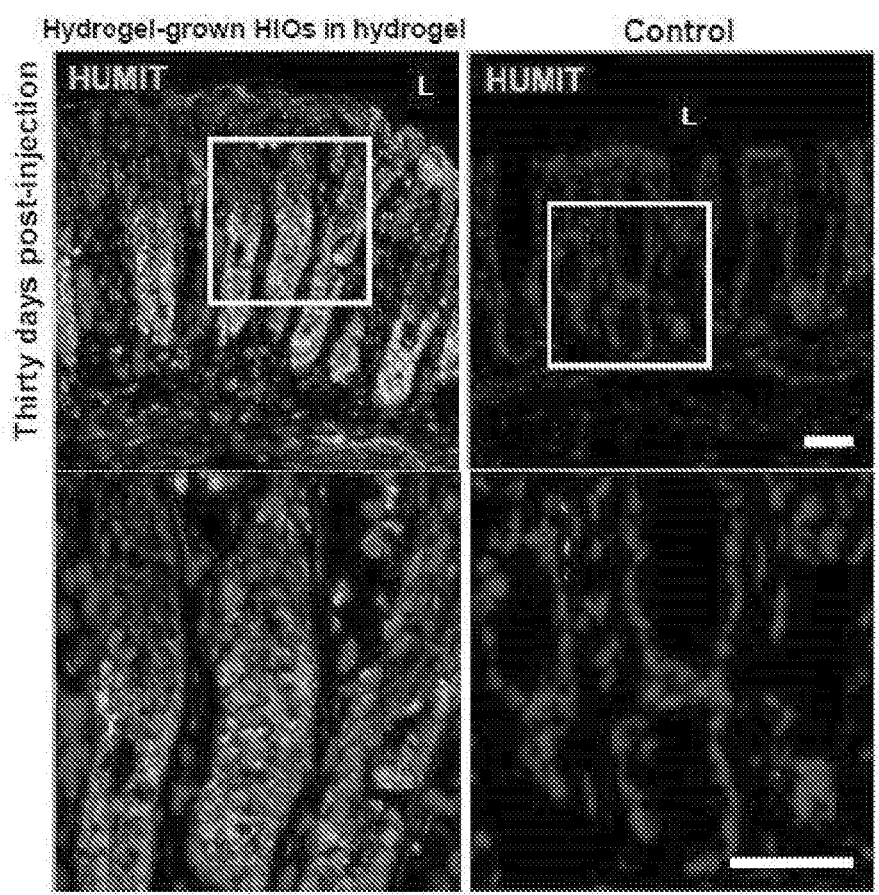
FIG. 16B depicts fluorescent microscopy images labeled for human mitochondria (HUMIT) of murine colonic tissue at the wound site at 4 weeks post-injection or control tissue. DAPI, counterstain. "L" indicates HIO lumen. Bars, 100 μm. (c,d) In situ hybridization images of control adult human colon or sections taken at the mouse colonic wound site stained for human OLFM4+ cells (FIG. 16C) or mouse Lgr5+ intestinal stem cells ((FIG. 16D). Bars, 50 μm. The results are representative of two different experiments performed with 4 mice per condition (five colonic wounds/injections per mouse).
Figure 16C:
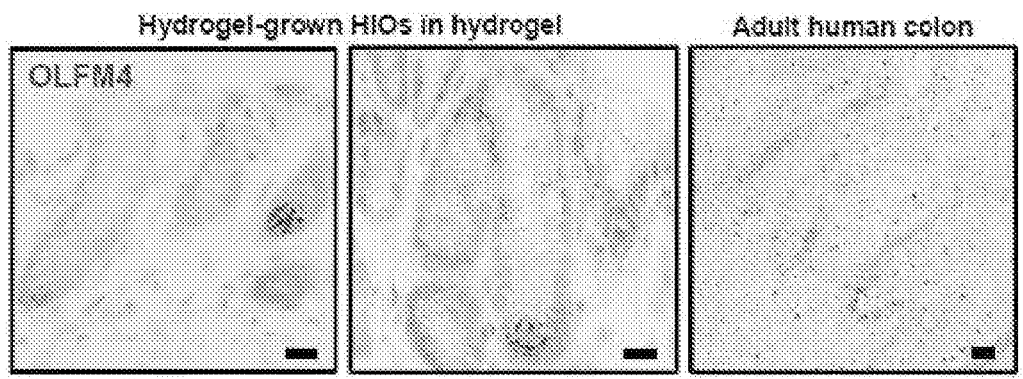
Figure 16D:
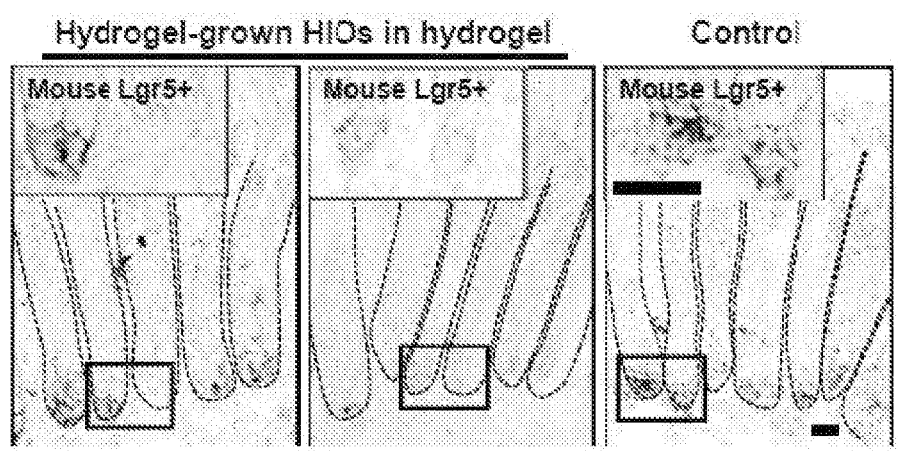

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Disclosed herein are synthetic hydrogels capable of supporting in vitro generation organoids from cellular spheroids, for instance, stem cell derived spheroids. The synthetic hydrogel are also useful as a storage matrix for spheroids and organoids, and can be used as a vehicle for the administration of such organoids and spheroids to a subject.

As used herein, the term spheroid (and cellular spheroid) refers to a plurality of cells grown in a 3-dimensional matrix. In contrast to cell cultures obtained from conventional two-dimensional techniques, spheroids can growth in all directions, and the resulting tissue more closely resembles the morphology of cells grown in vivo. As used herein, the term organoid (and cellular organoid) refers to a three-dimensional cell cultures that incorporate some of the key features of the represented organ. Unless specified to the contrary, an organoid may be obtained from adult stem cell-containing tissue samples, single adult stem cells, or from the directed differentiation of pluripotent stem cells, multipotent stem cells, or totipotent stem cells.

The synthetic hydrogels include a network of crosslinked hydrophilic polymer conjugated to adhesion peptides. Suitable hydrophilic polymers include polyalkylene glycol polymers, polyalkylene oxide homopolymers such as polypropylene glycols, polyoxyethylenated polyols, copolymers thereof and block copolymers thereof, as well as poly (oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. The molecular weight of the hydrophilic polymer can be from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer is a polyethylene glycol, i.e., PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In preferred embodiments, the crosslinked hydrophilic polymer is a branched or multi-arm polymer. As used herein, a multi-arm polymer describes a polymer having a central core with at least two polymers covalently attached thereto. Multi-arm polymers can have 2, 3, 4, 5, 6, 7, 8 or more polymer arms. Preferred multi-arm polymers, as defined above, include those with 4 arms. Generally, all of the polymers attached to the core are the same, but in some instances different hydrophilic polymers, as defined above, can be used. Suitable cores include those derived from polyols, including glycerol (3-arm), pentaerythritol (4-arm), tetraglycerol (6-arm), and hexaglycerol (8-arm). A particularly preferred polymer is a 4-arm PEG, having a total molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer network can have the general formula:

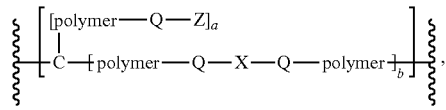

wherein 'polymer' in each case independently represents any hydrophilic polymer, including those defined above, C represents a core, Q represents a linker, Z represents an adhesion peptide, X represents a crosslinker, a is greater than 0, and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

In some embodiments, the hydrophilic polymer can be a poly(ethylene glycol), i.e., networks having the formula:

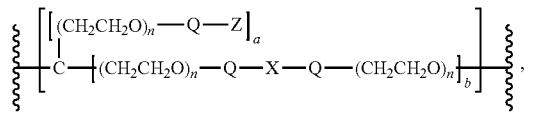

wherein C represents a core, n is an integer from 20-2,000, Q is a linking moiety, Z is an adhesion peptide, X is a crosslinker, a is greater than 0 and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

Suitable C groups can be derived from a polyol such as glycerol, pentaerythritol, sorbitol, mannitol, tetraglycerol, and hexaglycerol. In some instances, the core can have the general structure:

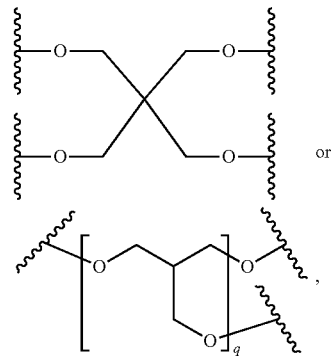

or wherein q is any integer, for instance 1, 2, 3, 4, 5, 6, 7, 8, 9, or 10 and □ represents a link to a hydrophilic polymer, as described above. Other suitable polyols include carbohydrates, including monosaccharides and di-saccharides, such as glucose, xylose, mannose, galactose, sucrose, maltose, trehalose and fructose, and cyclic polyols like cyclopropane-1,2,3-triol, cyclobutane-1,2,3,4-tetraol, cyclopentane-1,2,3,4-tetraol, cyclopentane-1,2,3,4,5-pentaol, cyclohexane-1,2,4,5-tetraol, cyclohexane-1,2,3,4,5,6-hexaol, and the like.

Suitable Q group include those formed via Michael addition between a nucleophilic group on the adhesion peptide or crosslinker, and a Michael acceptor bonded to the hydrophilic polymer. For instance, in some embodiments, Q represents a group having the formula:

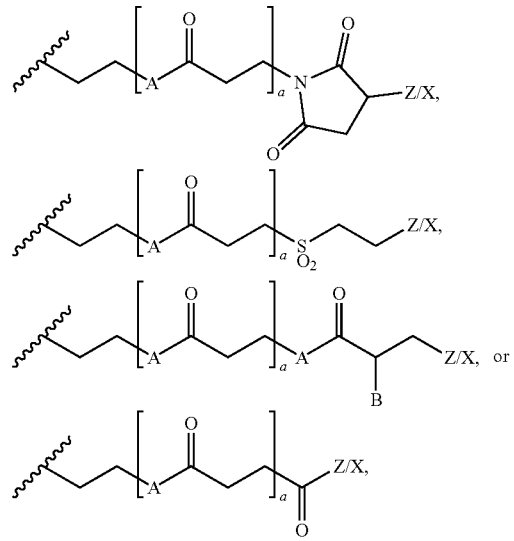

wherein A is independently selected from O or NH, a is independently selected from 0 or 1, B is selected from hydrogen or methyl, Z/X in each case independently represents either an adhesion peptide or crosslinker, and □ represents a link to a hydrophilic polymer, as described above.

In some embodiments, the adhesion peptide can include the sequence RGD. In some embodiments, the adhesion peptide can include GRGDSPC (SEQ. ID 1), CRGDS (SEQ. ID 2), CRGDSP (SEQ. ID 3), CPHSRN (SEQ. ID 4), CGWGGRGDSP (SEQ. ID 5), CGGSIDQVEPYSSTAQ (SEQ. ID 6), CGGRNIAEIIKDI (SEQ. ID 7), CGGDITYVRLKF (SEQ. ID 8), CGGDITVTLNRL (SEQ. ID 9), CGGRYVVLPR (SEQ. ID 10), CGGKAFDITYVRLKF (SEQ. ID 11), CGGEGYGEGYIGSR (SEQ. ID 12), CGGATLQLQEGRLHFXFDLGKGR, wherein X=Nle (SEQ. ID 13), CGGSYWYRIEASRTG (SEQ. ID 14), CGGGEFYFDLRLKGDKY (SEQ. ID 15), CKGGNGEPRGDTYRAY (SEQ. ID 16), CKGGPQVTRGDVFTMP (SEQ. ID 17), CGGNRWHSIYITRFG (SEQ. ID 18), CGGASIKVAVSADR (SEQ. ID 19), CGGTTVKYIFR (SEQ. ID 20), CGGSIKIRGTYS (SEQ. ID 21), CGGSINNNR (SEQ. ID 22), CGGSDPGYIGSR (SEQ. ID 23), CYIGSR (SEQ. ID 24), CGGTPGPQGIAGQGVV (SEQ. ID 25), CGGTPGPQGIAGQRVV (SEQ. ID 26), CGGMNYYSNS (SEQ. ID 27), CGGKKQRFRHRNRKG (SEQ. ID 28), CRGDGGGGGGGGGGGGPHSRN (SEQ. ID 29), CPHSRNSGSGSGSGSGRGD (SEQ. ID 30), Acetylated-GCYGRGDSPG (SEQ. ID 31), ((GPP)5GPC) (SEQ. ID 32), CRDGS (SEQ. ID 33), cyclic RGD{Fd}C (SEQ. ID 34), CGGRKRLQVQLSIRT (SEQ. ID 35), CIKVAV (SEQ. ID 36), CGGAASIKVAVSADR (SEQ. ID 37), CGGKRTGQYKL (SEQ. ID 38), CGGTYRSRKY (SEQ. ID 39), CGGYGGGP(GPP)5GFOGERPP(GPP)4GPC (SEQ. ID 40), CGGKRTGQYKLGSKTGPGQK (SEQ. ID 41), QAKHKQRKRLKSSC (SEQ. ID 42), SPKHHSQRARKKKNKNC (SEQ. ID 43), CGGXBBXBX, wherein B=basic residue and X=hydropathic residue (SEQ. ID 44), and CGGXBBBXXBX, wherein B=basic residue and X=hydropathic residue (SEQ. ID 45). In some preferred embodiments, the adhesion peptide includes the sequence GRGDSPC.

Suitable crosslinkers include enzymatically cleavable and non-cleavable peptide sequences. The peptide sequences will generally include a cysteine residue at each end of the sequence. Exemplary cleavable peptides include those that are cleavable by MMP, cathepsin, or other protease. Although the cysteine may be the final amino acid residue at each end of sequence, it is more preferable that the crosslinking peptides are terminated with a glycine or other inert residue. Suitable crosslinking peptides include the sequences GCRDGPQG↓IWGQDRCG (SEQ. ID 46), GCRDGPQG↓IAGQDRCG (SEQ. ID 47), GCRDVPMS↓MRGGDRCG (SEQ. ID 48), GCRDIPVS↓LRSGDRCG (SEQ. ID 49), GCRDRPFS↓MIMGDRCG (SEQ. ID 50), GCRDVPLS↓LTMGDRCG (SEQ. ID 51), GCRDVPLS-↓LYSGDRCG (SEQ. ID 52), GCRDIPES↓LRAGDRCG (SEQ. ID 53), GCRDSGESPAY↓YTADRCG (SEQ. ID 54), GCRDGGYAE↓LRMGGDRCG (SEQ. ID 55), GCRDGGPLG↓LYAGGDRCG (SEQ. ID 56), GCRDGPLG↓L-WARDRCG (SEQ. ID 57), wherein ↓ represents a cleavable amide bond. In some embodiments, the crosslinker is a not a peptide, for instance a di-mercapto compound such as a 1,4-dithiothreitol (1,4-dimercapto-2,3-butanediol) or poly (ethylene glycol) dithiol.

Aqueous compositions including the networks described above can be used as a support matrix or carrier for a variety of cellular structures. As used herein, cellular structures include stem cells, cell-derived spheroids, and organoids. For instance, the networks can be combined with organoids, for instance a lung organoid, cerebral organoid, thyroid organoid, thymic organoid, testicular organoid, hepatic organoid, pancreatic organoid, gut organoid (i.e., intestinal organoid, gastric organoid, or lingual organoid), epithelial organoid, lung organoid, renal organoid, embryonic organoid, or cardiac organoid. The hydrophilic networks can also be combined with cell-derived spheroids, e.g., pluripotent stem cells like embryonic stem cells and induced pluripotent stem cells. In some cases, stem cells such as multipotent stem cells, totipotent stem cells, pluripotent stem cells, embryonic stem cell, induced pluripotent stem cells, extra-embryonic fetal stem cells, amniotic stem cells (including cells stem cells obtained from the cord blood), and adult stem cells (including, but not limited to hematopoietic stem cells, endothelial stem cells, intestinal stem cells, mammary stem cells, neural stem cells, and mesenchymal stem cells) can be incorporated into the hydrogel.

The compositions can include water in an amount of at least 70% by weight relative to the total weight of the composition. In some embodiments, the water can be present in an amount of at least 75%, at least 80%, at least 85%, at least 87.5%, at least 90%, at least 92.5%, or at least 95% by weight relative to the total weight of the composition. In some embodiments, the compositions will include the hydrophilic crosslinked polymer network in an amount no greater than 30%, no greater than 25%, no greater than 20%, no greater than 15%, no greater than 12.5%, no greater than 10%, no greater than 7.5%, or no greater than 5%, by weight relative to the total volume of the hydrogel. In certain embodiments, the crosslinked hydrophilic polymer network is present in an amount from 1-8%, from 2-7%, from 2-6%, from 3-6%, from 3-5%, or from 3.5-4.5% polymer weight by total volume of the composition. In certain embodiments, the crosslinked hydrophilic polymer network is present in an amount of about 4% polymer weight by total volume of the composition.

The crosslinked networks disclosed herein may be prepared by first conjugating an adhesion peptide to a hydrophilic polymer having the formula:

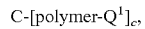
C-[polymer-$Q^1$]$_c$, wherein C and "polymer" are as defined above, c is an integer greater than or equal to 3, and $Q^1$ is an electrophilic group capable of reacting with a thiol group. In some embodiments, the hydrophilic polymer is PEG, i.e., a compound of formula:

C—[(CH$_2$CH$_2$O)$_n$-$Q^1$]$_c$, wherein C, n, c, and $Q^1$ are as defined above. In some embodiments, $Q^1$ represents a group having the formula:

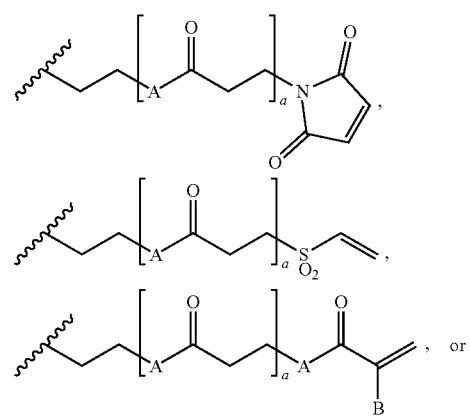

-continued

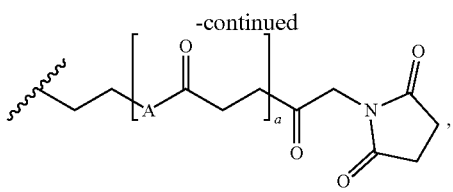

wherein A is independently selected from O or NH, a is independently selected from 0 or 1, B is selected from hydrogen or methyl, and □ represents a link to a hydrophilic polymer, as described above.

The adhesion peptide can contain a single cysteine residue or thiol group, and will be combined such that there is a molar excess of $Q^1$ groups relative to cysteine/thiol groups. For instance, molar ratio of $Q^1$ groups to cysteine/thiol residues is from 10:1 to 1.5:1, from 8:1 to 1.5:1, from 6:1 to 1.5:1, from 4:1 to 1.5:1, from 3:1 to 1.5:1, from 2.5:1 to 1.5:1, from 5:1 to 2:1, from 5:1 to 3:1, or from 5:1 to 4:1. The molar ratio of nucleophilic groups in the crosslinker to unreacted $Q^1$ groups (assuming complete reaction with adhesion peptide) can be 1:1, greater than 1:1, e.g., 1.1:1, 1.2:1, or 1.5:1, less than 1:1, e.g., 0.9:1, 0.8:1, or 0.5:1, from 0.5:1 to 1.5:1, from 0.75:1 to 1.25:1, from 0.5:1 to less than 1:1, or from 1.5:1 to greater than 1:1.

Each of the hydrophilic polymer, adhesion peptide, crosslinker, and cellular component can be separately combined with an appropriate aqueous solution, generally buffered to a pH from 7.0-8.0, from 7.2-7.6, or 7.3-7.5. Any physiologically compatible buffer may be used, such as 4-(2-hydroxyethyl)piperazine-1-ethanesulfonic acid (HEPES), phosphate buffers, carbonate buffers, tromethamine (tris) buffers, including those formed with EDTA and an acid such as acetic acid, boric acid, and the like.

The relative ratios of the components may be as follows:

| Hydrogel component | Volume fraction of hydrogel component | Concentration factor of hydrogel component |
| --- | --- | --- |
| Hydrophilic polymer | 0.3-0.5 | 2.5X |
| Adhesion peptide | 0.15-0.25 | 5X |
| Crosslinker | 0.15-0.25 | 5X |
| Cellular structure | 0.15-0.25 | 5X |

The hydrophilic polymer may be combined with a solution of adhesive peptide such that the final adhesive peptide concentration is from 0.1-100 mM, from 0.5-75 mM, from 1-50 mM, from 5-25 mM, or from 7.5-15 mM, based on the total volume of the hydrogel. The mixture can be incubated at a temperature from 23-50° C., from 28-45° C., from 32-40° C., or at 37° C. for at least 5 minutes, at least 10 minutes, at least 15 minutes, or at least 20 minutes. The resulting product is designated the hydrogel precursor, which has the following structure:

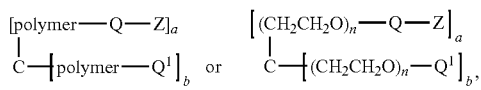

wherein C, 'polymer,' n, Q, $Q^1$, Z, a, and b have the meanings given above. The hydrogel precursor may be directly converted to a hydrogel by combination with the crosslinker, or may first be combined with a cellular structure and subsequently combined with the crosslinker to form the hydrogel.

Stem cells can be cultured and differentiated into tissue spheroids, and organoids can be obtained from iPSCs or ESCs and Matrigel using established methods. The spheroids and organoids can be suspended in a growth medium appropriate for the tissue type. The suspension can then be combined with the hydrogel precursor solution and combined with a solution of crosslinker. Generally, crosslinker solution is placed in the center of a dish, and then combined with the hydrogel precursor/cell suspension. It is important to mix the components thoroughly. The mixture can be incubated at a temperature from 23-50° C., from 28-45° C., from 32-40° C., or at 37° C. for no more than 5 minutes, no more than 10 minutes, no more than 20 minutes, no more than 30 minutes, or no more than 60 minutes to generate the hydrogel, which is then overlaid with additional growth medium. The growth medium should be replaced every 3-5 days. Spheroids and organoids stored in the hydrogel matrix are stable over prolonged periods of time. Suitable spheroids that can be employed with the hydrogel matrix include round spheroids, mass spheroids, grape-like spheroids, and stellate spheroids. The round spheroids usually express tight cell junction proteins such as ZO-1. Colonies of round spheroids sometimes undergo lumen formation in the center, which usually occurs in a time-dependent manner. The mass-type spheroids are characterized by round colony outlines, disorganized nuclei, filled colony centers, and strong cellular communication. The mass spheroids are usually larger in diameter than round spheroids and overexpress luminal keratin 8 (KRT8) and keratin 18 (KRT18), yet lack a lumen. The grape-like spheroids display a distinguished grape-like appearance and usually have poor cell-cell interactions. The stellate-type spheroids are characterized by their invasive phenotype with stellate projections that often bridge multiple colonies and/or invade the matrixes Organoids grown in the hydrogel matrix may be passaged using conventional techniques. Generally, the organoids are mechanically dislodged from the hydrogel by vigorously pipetting. Any remaining hydrogel still adhering to the organoid can be removed with forceps. The organoid is then cut in half, and each half resuspended in growth medium. Each half may be combined with hydrogel precursor solution and cast into hydrogels as described above. In this fashion, larger organoids may be obtained.

The compositions disclosed herein may be used to promote wound healing and tissue repair. In addition to the organoid, the hydrogel composition may further include additional therapeutics to facilitate healing and prevent infection. Suitable additional therapeutics include growth factors, antibiotics, antivirals, analgesics, cytokines, enzymes, aptamers, nucleic acids, and combinations thereof.

In some instances, a preformed hydrogel/organoid composition may be directly contacted with the site of tissue injury. In other instances, the composition may be administered subcutaneously adjacent or proximate to the injury. In some embodiment the hydrogel precursor is combined with the crosslinker at the site of injury at the time of administration. A preferred method includes an in vivo hydrogel formation. The hydrogel precursor/organoid is loaded into a dispensing means, for instance a syringe, which is in fluid communication with a needle by way of a tube. Inside the tube is loaded the crosslinker, such that when the hydrogel precursor/organoid is expelled from the syringe, it combines with the crosslinker solution and is ejected from the needle into the directed site.

EXAMPLES

The following examples are for the purpose of illustration of the invention only and are not intended to limit the scope of the present invention in any manner whatsoever.

Immunofluorescence Analysis

For immunofluorescence labeling of frozen sections from colon, HIOs, kidney capsule implanted-HIOs or HLOs, these were fixed with 3.7% (w/v) paraformaldehyde at room temperature for 15 min, followed by 0.5% (w/v) Triton X-100 for 5 min. Primary antibody incubation was performed overnight at a 1:100 dilution, unless stated otherwise. Secondary antibody incubation was performed for 1 h at a 1:2000 dilution. Detailed information on the antibodies used including their resources (company names, catalogue numbers) and dilutions are provided in the Reporting Summary.

Differentiation of hPSCs Into Intestinal Spheroids or HLOs

All work using human pluripotent stem cells was approved by the University of Michigan Human Pluripotent Stem Cell Oversight Committee (HPSCRO). Stem cell lines are routinely monitored for chromosomal karyotype, pluripotency (using a panel of antibody and RT-qPCR markers), and for the ability to undergo multi-lineage differentiation. For intestinal spheroid generation, mycoplasma-free human ES cells (H9, NIH registry #0062) and iPS cells were cultured on Matrigel™-coated plates and differentiated into intestinal tissue. Floating spheroids present in the cultures on day 4 and day 5 of mid/hindgut induction were harvested for use in subsequent experiments. In some experiments, hESCs expressing a constitutively active H2BmCherry fluorescent reporter were used. This line was generated by infecting hESCs with a lentivirus containing PGK-H2BmCherry. For HLO generation, human ES cells (UM63-1, NIH registry #0277) were maintained, differentiated and expanded into HLOs.

Hydrogel Formation and In Vitro Intestinal Spheroid/HIO

To prepare PEG hydrogels, PEG-4MAL macromer (MW 22,000 or 44,000; Laysan Bio) was dissolved in 4-(2-hydroxyethyl)piperazine-1-ethanesulfonic acid (HEPES) buffer (20 mM in DPBS, pH 7.4). Adhesive and GPQ-W crosslinking peptides were custom synthesized by AAPPTec. Adhesive peptides RGD (GRGDSPC), AG73 (CGGRKRLQVQLSIRT), GFOGER (GYGGGP(GPP)$_5$GFOGER (GPP)$_5$GPC), IKVAV (CGGAASIKVA-VSADR) and RDG (GRDGSPC) were dissolved in HEPES at 10.0 mM (5× final ligand density) and mixed with PEG-4MAL at a 2:1 PEG-4MAL/ligand ratio to generate functionalized PEG-4MAL precursor. Bis-cysteine crosslinking peptide GPQ-W (GCRDGPQG↓IWGQDRCG; ↓ denotes enzymatic cleavage site) or non-degradable crosslinking agent DTT (1,4-dithiothreitol; 3483-12-3, Sigma) was dissolved in HEPES at a density corresponding to 1:1 maleimide/cysteine ratio after accounting for maleimide groups reacted with adhesive peptide. For HIOs encapsulation, spheroids were embedded and expanded in Matrigel™ for up to 30 d. Resulting HIOs were dislodged from the Matrigel™ and resuspended at 5× final density (final density: 2-4 HIOs/hydrogel) in intestine growth medium[38] and kept on ice. For human intestinal spheroid encapsulation, spheroids were harvested immediately after differentiation and were resuspended at 5× final density (final density: 20-30 spheroids/hydrogel) in intestine growth medium and kept on ice. For HLOs encapsulation, these were dislodged from the Matrigel™ and resuspended at 5× final density (final density: 2-4 HLOs/hydrogel) in foregut growth medium and kept on ice. To form hydrogels, adhesive peptide-functionalized PEG-4MAL macromer, cells, and crosslinking peptide were polymerized for 20 min before addition of intestine growth medium. Matrigel™-generated hPSC-derived HIOs were generated and cultured. Passaging of HIOs cultured in PEG-4MAL hydrogels was performed similarly to tissue embedded in Matrigel™ Briefly, HIOs were dislodged from the PEG-4MAL hydrogel, transferred to a sterile Petri dish, and manually cut into halves using a scalpel. HIO halves were resuspended at 5× final density (final density: 2-4 HIOs/hydrogel) in intestine growth medium and mixed with hydrogel precursor solutions to form PEG-4MAL hydrogels. HIOs were passaged up to 3 times over the course of 3 weeks.

Hydrogel Characterization

The storage and loss moduli of hydrogels were assessed by dynamic oscillatory strain and frequency sweeps performed on a MCR 302 stress-controlled rheometer (Anton Paar) with a 10-mm diameter, 2° cone, and plate geometry (CP 10-2, Anton Paar). Oscillatory frequency sweeps were used to examine the storage and loss moduli ($\omega$=0.5–100 rad s$^{-1}$) at a strain of 2.31%.

Viability Assay and Quantification

PEG-4MAL gels were incubated in 2 μM calcein-AM (live; Life Technologies), and 1 μm TOTO-3 iodide (dead; Life Technologies) in growth medium for 1 hr. Samples were imaged using an Axiovert 35, Zeiss microscope. Quantification of viability was performed by calculating the percentage of the total projected area of a spheroid/organoid that stained positive for the live or dead stain using ImageJ (National Institute of Health, USA).

Inhibition of Mediators of Mechanotransduction

Inhibition of YAP, myosin II or Rho-associated kinase was performed using verteporfin (SML0534, Sigma), blebbistatin (203389, Calbiochem) and Y-27632 (688002, Calbiochem), respectively, by adding 10 or 30 μM to the intestine growth medium 20 min after spheroid encapsulation in hydrogel. Cell apoptosis/death was assessed 1 d after encapsulation using Annexin V/Dead Cell Apoptosis Kit (A13201, ThermoFisher). Samples were imaged using an Axiovert 35, Zeiss microscope.

RT-qPCR

Total RNA from hESC day 0 spheroids or HIOs grown in PEG-4MAL hydrogels or Matrigel™ was extracted using the MagMax RNA isolation system and MagMax-96 total RNA isolation Kit (AM1830, ThermoFisher Scientific). cDNA was synthesized using the SuperScript VILO cDNA Synthesis Kit (11754-250, ThermoFisher Scientific). RT-qPCR was carried out using the QuantiTect SYBR Green PCR Kit (204145, Qiagen). Relative gene expression was plotted as Arbitrary Units using the formula: [2^(housekeeping gene Ct−gene of interest Ct)]×10,000.

| Primer sequences for RT-qPCR | | |
|---|---|---|
| Human gene | Forward primer | Reverse primer |
| 4-Oct | gtggaggaagctgacaacaa | ggttctcgatactggttcgc |
| FOXA2 | cgactggagcagctactatgc | tacgtgttcatgccgttcat |
| CDX2 | gggctctctgagaggcaggt | ggtgacggtgggttagca |
| ECAD | ttgacgccgagagctacac | gaccggtgcaatcttcaaa |
| CLDN2 | aaggctctgcaaagaactgc | ctgccaggctgacttctctc |
| ZO1 | gggaacaacatagagtgacgc | ccccactctgaaaatgagga |

Animal Models

All animal studies were conducted following approved protocols established by University of Michigan's Institutional Animal Care and Use Committee (IACUC) in accordance with the U.S. Department of Agriculture (USDA) Animal and Plant Health Inspection Service (APHIS) regulations and the National Institutes of Health (NIH) Office of Laboratory Animal Welfare (OLAW) regulations governing the use of vertebrate animals. Male (8 weeks old) NOD-scid IL2Rg-null (NSG) mice (Jackson Laboratory) were used for all our experiments.

Kidney Capsule Implantation

Organoids were implanted under the kidney capsule of male NOD-scid IL2Rg-null (NSG) mice (Jackson Laboratory). Briefly, mice were anesthetized using 2% isofluorane. The left flank was shaved and sterilized using chlorhexidine and isopropyl alcohol. A left flank incision was used to expose the kidney. HIOs were manually placed in a subcapsular pocket of the kidney using forceps. An intraperitoneal flush of Zosyn (100 mg/kg; Pfizer) was administered prior to closure in two layers. The mice were sacrificed and transplant retrieved after 12 weeks. The results are representative of one experiment performed with 3 mice per condition (one organoid implanted per kidney capsule).

Colonic Mucosal Wound and HIO Injections

NSG mice were anesthetized by intraperitoneal injection of a ketamine (100 mg/kg)/xylazine (10 mg/kg) solution. A high-resolution miniaturized colonoscope system equipped with biopsy forceps (Coloview Veterinary Endoscope, Karl Stortz) was used to biopsy-injure the colonic mucosa at 3-5 sites along the dorsal artery. Wound size averaged approximately 1 mm$^2$. HIO injection was performed on day 1 after wounding with the aid of a custom-made device comprising a 27-gauge needle (OD: 0.41 mm) connected to a small tube. Endoscopic procedures were viewed with high-resolution (1,024×768 pixels) live video on a flat-panel color monitor.

Wound Closure Quantification

Mice were anesthetized by intraperitoneal injection of a ketamine (10 g/1) xylazine (8 g/1) solution (10 µl/g body weight). To create mucosal injuries in the mouse colon and to monitor their regeneration, a high-resolution colonoscopy system was used. Each wound region was digitally photographed at day 1 and day 5, and wound areas were calculated using ImageJ (National Institute of Health, USA).

In Situ Hybridization (ISH)

ISH for mouse Lgr5 expression was performed on frozen sections fixed with 4% paraformaldehyde (PFA). Slides were permeabilized with proteinase K (3115887001, Sigma-Aldrich) for 30 min at 37° C., washed with Saline-Sodium Citrate buffer and then acetylated at room temperature for 10 min. Pre-hybridization step was performed for 1 h at 37° C. in a humidified chamber. A DIG-labeled riboprobe diluted in hybridization buffer was incubated overnight at 68° C. The slides were then washed and blocked for 1 h at room temperature followed by incubation with DIG antibody (11093274910, Sigma-Aldrich) overnight at 4° C. The developer solution (11681451001, Roche) was incubated for 72 h until the Lgr5 cells became evident. ISH for OLFM4 was performed using the RNAscope 2.5 HD manual assay with brown chromogenic detection (Advanced Cell Diagnostics, Inc.) per manufacturer's instructions. The human 20 base pair OLFM4 probe was generated by Advanced Cell Diagnostics targeting 20 base pairs within 1111-2222 of OLFM4 (gene accession NM_006418.4) and is commercially available.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A composition comprising a cellular structure dispersed in a hydrogel matrix, wherein the hydrogel matrix comprises a crosslinked hydrophilic polymer network covalently bonded to a plurality of adhesion peptides, wherein the cellular structure comprises an organoid, cellular spheroid, pluripotent stem cell, or a combination thereof.

2. The composition according to claim 1, wherein the cellular structure comprises an organoid, cellular spheroid, or combination thereof.

3. The composition of claim 2, wherein the cellular structure comprises an organoid comprising an intestinal organoid, gastric organoid, or lingual organoid.

4. The composition according to claim 1, wherein the crosslinked hydrophilic polymer network has the general formula:

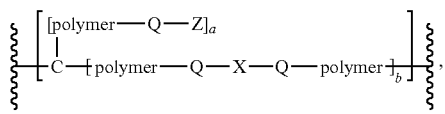

wherein 'polymer' represents any hydrophilic polymer, C represents a core, Q represents a linker, Z represents an adhesion peptide, X represents a crosslinker, a is greater than 0, and b is greater than 1.

5. The composition according to claim 4, wherein the hydrophilic polymer comprises a multi-armed poly(ethylene glycol).

6. The composition according to claim 4, wherein the crosslinked hydrophilic polymer network has the general formula:

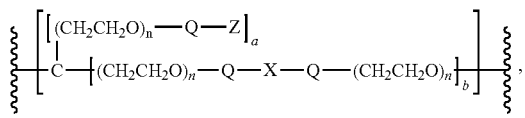

wherein C represents a core, n is an integer from 20-2,000, Q is a linking moiety, Z is an adhesion peptide, X is a crosslinker, a is greater than 0 and b is greater than 1, provided the sum of a+b does not exceed 7.

7. The composition according to claim 4, wherein C represents a group having the formula:

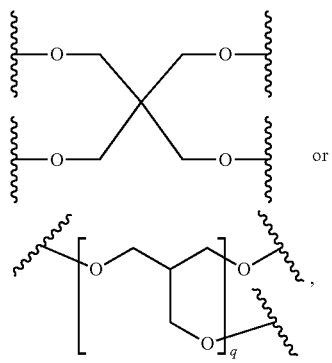

wherein q is 1, 2, 3, 4, 5, or 6.

8. The composition according to claim 4, wherein Q represents a group having the formula:

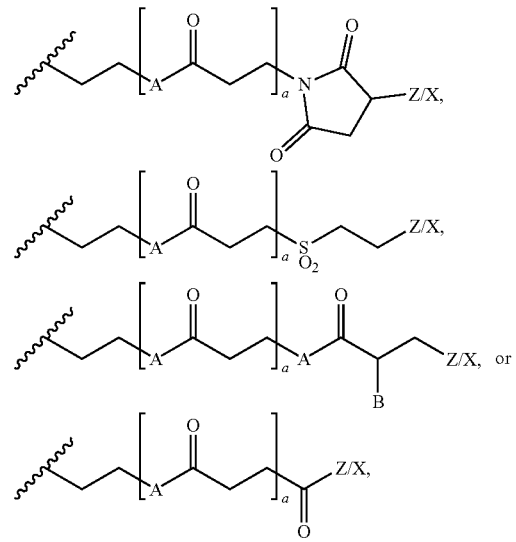

wherein A is independent selected from O or NH, a is independently selected from 0 or 1, B is selected from hydrogen or methyl, and Z/X in each case independently represents either an adhesion peptide or crosslinker.

9. The composition according to claim 1, wherein the adhesion peptide comprises the amino acid sequence RGD.

10. The composition according to claim 9, wherein the adhesion peptide comprises the amino acid sequence GRGDSPC (SEQ. ID NO: 1).

11. The composition according to claim 1, wherein the crosslinked hydrophilic polymer is crosslinked with a crosslinker comprising a MMP- or cathepsin- or other protease-cleavable or non-cleavable peptide comprising at least a cysteine residue at each end of the sequence.

12. The composition according to claim 1, wherein the crosslinker comprises 1,4-dithiothreitol poly(ethylene glycol) dithiol.

13. The composition according to claim 1, wherein the crosslinked hydrophilic polymer network is present, on a dry basis, in an amount from 1-8% polymer weight by total volume of the composition.

14. The composition according to claim 1, wherein the crosslinked hydrophilic polymer is present in an amount of no greater than 15%, by weight relative to the total volume of the composition.

15. A composition according to claim 1, obtained by dispersing an organoid in a hydrogel matrix, wherein the hydrogel matrix is obtained by crosslinking a hydrophilic polymer conjugated to a plurality of adhesion peptides.

16. A method of generating an organoid, comprising contacting the composition of claim 1 and a growth medium.

17. A method of repairing a tissue injury, comprising contacting the injured tissue with the composition according to claim 1.

18. A method of repairing a tissue injury comprising combining a solution comprising an organoid and a hydrogel precursor having the formula:

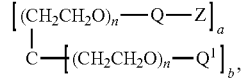

wherein C represents a core, n is an integer from 20-2,000, Q is a linking moiety, Z is an adhesion peptide, X is a crosslinker, a is greater than 0 and b is greater than 1 $Q^1$ is an electrophilic group capable of reacting with a thiol group; with a solution comprising a crosslinker; and contacting injured tissue with the resulting mixture.

19. An organoid delivery device comprising:
a) a syringe comprising a hydrogel precursor and organoid;
b) a mixing vessel comprising a crosslinking; and
c) an injection needle;
 wherein the syringe is in fluid communication with the mixing vessel and injection needle, in which the mixing vessel is disposed between the needle and syringe.

* * * * *